US007871604B1

(12) United States Patent
Curtiss, III et al.

(10) Patent No.: US 7,871,604 B1
(45) Date of Patent: Jan. 18, 2011

(54) RECOMBINANT BACTERIAL VACCINE SYSTEM WITH ENVIRONMENTALLY LIMITED VIABILITY

(75) Inventors: Roy Curtiss, III, St. Louis, MO (US); Steven A. Tinge, Belleville, IL (US)

(73) Assignee: Washington University, St. Louis, MO (US)

( * ) Notice: Subject to any disclaimer, the term of this patent is extended or adjusted under 35 U.S.C. 154(b) by 1537 days.

(21) Appl. No.: 09/120,970

(22) Filed: Jul. 22, 1998

Related U.S. Application Data

(63) Continuation of application No. 08/473,789, filed on Jun. 7, 1995, now abandoned.

(51) Int. Cl.
*C12N 1/21* (2006.01)
*A01N 63/00* (2006.01)

(52) U.S. Cl. .............. 424/93.1; 424/93.48; 424/257.1; 424/258.1; 435/69.1; 435/252.3; 435/442; 435/471

(58) Field of Classification Search .............. 424/200.1, 424/234.1, 92, 258.1, 252.8, 257.1, 93.1, 424/93.2, 93.48; 530/351; 435/69.7, 5, 325, 435/252.1, 252.33, 320.1, 879, 442, 471, 435/481, 69.1; 514/44, 12
See application file for complete search history.

(56) References Cited

U.S. PATENT DOCUMENTS 4,190,495 A    2/1980   Curtiss (Continued)

FOREIGN PATENT DOCUMENTS

EP    0 381 706 B1    4/1995
GB    1516458    *    9/1976

WO    WO 95/14091    5/1995

OTHER PUBLICATIONS

Curtiss et al, Immunological Investigations, Jan.-May 1989, vol. 18(1-4), pp. 583-589.*

(Continued)

*Primary Examiner*—Robert B Mondesi
*Assistant Examiner*—Ginny Portner
(74) *Attorney, Agent, or Firm*—Yankwich & Associates, P.C.; Leon R. Yankwich; Michael R. Wesolowski

(57) ABSTRACT

Disclosed is an Environmentally Limited Viability System (ELVS) for microorganisms based on temperature differences between permissive and non-permissive environments. Viability of the microorganisms are limited to the permissive environment by specifically expressing one or more essential genes only in the permissive environment, or expressing one or more lethal genes only in the non-permissive environment. Environmentally Limited Viability Systems are also disclosed involving coordinate expression of a combination of required genes and lethal genes. Microorganisms containing an Environmentally Limited Viability System are useful for release into a permissive environment. Temperature regulated Environmentally Limited Viability Systems are particularly suited for use with recombinant avirulent *Salmonella* vaccines by limiting their growth to the warmer environment inside the host. Such vaccines can be administered to protect humans or warm-blooded animals against bacterial, viral, mycotic and parasitic pathogens, especially those that colonize on or invade through mucosal surfaces. This antigen delivery system can also be used for expression of gamete-specific antigens to induce immune responses to block fertilization, or to induce immune responses to tumor antigens. In the event that an individual sheds live vaccine into the environment, the presence of the ELVS prevents survival of the vaccine. When environmentally regulated lethal genes are present on an extrachromosomal element and are regulated by chromosomal genes, transfer of the extrachromosomal element to other microorganisms will be limited by unregulated expression of the lethal genes in the recipient microorganism.

32 Claims, 6 Drawing Sheets

U.S. PATENT DOCUMENTS

| | | | | |
|---|---|---|---|---|
| 4,436,815 | A | * | 3/1984 | Hershberger et al. ......... 435/172 |
| 4,506,013 | A | * | 3/1985 | Hershberger et al. .......... 435/34 |
| 4,650,761 | A | * | 3/1987 | Hershberger et al. .......... 435/34 |
| 4,968,619 | A | * | 11/1990 | Curtiss, III ............. 435/252.33 |
| 5,190,931 | A | | 3/1993 | Inouye |
| 5,196,317 | A | * | 3/1993 | Heinrich et al. ............. 435/69.1 |
| 5,294,441 | A | * | 3/1994 | Curtiss, III ............... 424/200.1 |
| 5,316,933 | A | * | 5/1994 | Yoshimatsu et al. ......... 435/352 |
| 5,387,744 | A | * | 2/1995 | Curtiss, III ............... 424/235.1 |
| 5,468,485 | A | * | 11/1995 | Curtiss, III ............... 424/184.1 |
| 5,656,488 | A | * | 8/1997 | Curtiss, III ............. 435/252.33 |
| 5,672,345 | A | * | 9/1997 | Curtiss, III ................. 424/93.2 |
| 5,681,745 | A | * | 10/1997 | Szafranski et al. .......... 435/325 |
| 5,686,580 | A | * | 11/1997 | Fasano et al. ............ 530/389.5 |
| 5,695,983 | A | * | 12/1997 | Miller et al. ............. 435/252.8 |
| 5,702,916 | A | * | 12/1997 | Molin et al. ............... 435/69.1 |
| 5,733,760 | A | * | 3/1998 | Lu et al. ...................... 435/477 |
| 5,747,028 | A | * | 5/1998 | Calderwood et al. ....... 424/93.2 |
| 5,840,483 | A | * | 11/1998 | Curtiss, III ...................... 435/6 |
| 5,843,426 | A | * | 12/1998 | Miller et al. ............... 424/93.2 |
| 5,843,702 | A | * | 12/1998 | McConnell et al. ........ 435/69.1 |
| 5,855,879 | A | * | 1/1999 | Curtiss, III .................. 424/952 |
| 5,855,880 | A | * | 1/1999 | Curtiss et al. .............. 424/93.2 |
| 6,010,901 | A | * | 1/2000 | Miller, III et al. ........ 435/320.1 |
| 6,024,961 | A | * | 2/2000 | Curtiss, III et al. ....... 424/200.1 |
| 6,316,609 | B1 | * | 11/2001 | Dillon et al. ............... 536/23.1 |
| 6,610,529 | B1 | * | 8/2003 | Curtiss et al. ............ 435/252.3 |
| 6,780,405 | B1 | * | 8/2004 | Curtiss et al. .............. 424/93.1 |
| 2003/0082511 | A1 | * | 5/2003 | Brown et al. .................... 435/4 |
| 2003/0157071 | A1 | * | 8/2003 | Wolfe et al. ............. 424/93.21 |

OTHER PUBLICATIONS

Cieslak, PR et al, Vaccine, vol. 11(7). pp. 773-776, 1993.*
Gentry-Weeks, CR et al, Journal of Bacteriology, vol. 174(23), pp. 7729-7742, Dec. 1992.*
Jagusztyn-Krynicka, EK et al, Mar. 1993, vol. 61(3), pp. 1004-1015.*
Miller, IA et al, Mol. Gen. Genet, vol. 215, pp. 312-316, Jan. 1989.*
Nakayama et al, Bio/Technology, vol. 6, pp. 693-697, 1988.*
Schodel, F et al, Developments in biological standardization, vol. 82; pp. 151-158, 1994.*
Schodel, F et al, Infection Immunity, May 1994, vol. 62(5), pp. 1669-1676.*
Youderian, P et al, Virology, vol. 107(1), pp. 258-269, 1980.*
Schodel, F e tal, Developments in biological standarizaiton, 1994, vol. 82, pp. 151-158 (abstract).*
Redman, TK et al, Infection and Immunity, Aug. 1994, vol. 62(8), pp. 3162-3171 (abstract only).*
Schodel, F et al, Infection and Immunity, May 1994, vol. 62(5), pp. 1669-1676 (abstract only).*
Curtiss, R et al, Immunological investigations, Jan.-May 1989, vol. 18(1-4), pp. 583-596 (abstract only).*
Curtiss III, R, Release of Genetically engineered microorganisms, Chapter 2, pp. 7-20, 1988, Engineering organisms for safely: what is necessary(query)-genetically engineered microorganism relase in the environment; recombinant vaccine construction.*
Curtiss III, Roy, Genetic Manipulation of microorganisms: Potential benefits and biohazards, pp. 507-533, Ann. Rev. Microbiol. 1976, vol. 30, pp. 507-533.*
Barrett, *Textbook of Immunology*, Fourth Edition (C.V. Mosby Co., St. Louis, MO 1983).
Bienkowska-Szewczyk et al., The R Gene Product of Bacteriophage λ. *Mol. Gen. Genet.* 184:111-114 (1981).
Bochner et al., Positive Selection for Loss of Tetracycline Resistance, *J. Bacteriol.* 143:926 (1980).
Cardenas and Clements, Oral Immunization Using Live Attenuated *Salmonella* spp. as Carriers of Foreign Antigens, *Clinical Micro. Rev.* 5(31:328-342 (1992).
Cardineau and Curtiss, Nucleotide Sequence of the asd Gene of *Streptococcus mutans*, *J. Bio. Chem.* 262:33440-3353 (1987).

Chatfield et al., Construction of a Genetically Defined *Salmonella typhi* Mutant for the Engineering of a Candidate Oral Typhoid-Tetanus Vaccine, *Vaccine* 10:53-80 (1992).
Chatfield et al., The Development of Oral Vaccines Based on Live Attenuated *Salmonella* Strains, *FEMS Immunol. Med. Microbiol.* 7:107 (1993).
Christie et al., Synthetic Sites for Transcription Termination and a Functional Comparison with Tryptophan Operon Termination Sites In Vitro, *Proc. Natl. Acad. Sci. USA* 78:4180-4184 (1981).
Clements, Use of Attenuated Mutants of *Salmonella* As Carriers for Delivery of Heterologous Antigens to the Secretory Immune System, *Pathol. Immunopathol. Res.* 6:137-146 (1987).
Contreras et al., *Appl. Microbiol. Biotechnol.* 57(5):1504-1508 (1991).
Cornelis, Yersiniae, Finely Tuned Pathogens, *Molecular Biology of Bacterial Infections* (Cambridge University Press, Cambridge, 1992).
Curtiss, Engineering Organisms for Safety: What is Necessary: *The Release of Genetically-Engineered Micro-Organisms*, M. Sussman, et al., editor, Academic Press, 7-20 (1988).
Curtiss, Genetic Manipulation of Microorganisms: Potential Benefits and Biohazards, *Ann. Rev.* 30:507-533 (1976).
Curtiss et al., Research on Bacterial Conjugation with Mini-Cells and Minicell-Producing *E. Coli* Strains, *Microbial Drug Resistance* 3:169-183 (1982).
Curtiss et al., *Salmonella typhimurium* Deletion Mutants Lacking Adenylate Cyclase and Cyclic AMP Receptor Protein Are avirulent and Immunogenic, *Infect. Imm.* 553035-3043 (1987).
Curtiss et al., Chromosomal Aberrations Associated with Mutants to Bacteriophage Resistance in *Escherichia Coli*, *J. Bacteriol.* 89:28-40 (1965).
Curtiss et al., Avirulent *Salmonella* Expressing virulence Antigens from other Pathogens for use as Orally Administered Vaccines, *Virulence Mechanisms of Bacterial Pathogens*, (Roth, American Society for Microbiology, Washington, D.C. 1988) pp. 311-328.
Curtiss et al., Recombinant *Salmonella* Vectors in Vaccine Development, *Dev. Biol. Stand.* 82:23-33 (1994).
Curtiss et al., Stable Recombinant Avirulent *Salmonella* Vaccine Strains, *Adv. Exp. Med. Biol.* 251:33-47 (1989).
Curtiss, Attenuated *Salmonella* Strains as Live Vectors for the Expression of Foreign Antigens, *New Generation Vaccines* (Woodrow and Levine, eds. Marcel Dekker, New York, 1990) pp. 161-188.
Doggett and Curtiss Delivery of Antigens by Recombinant Avirulent *Salmonella* Strains, *Adv. Exp. Med. Biol.* 327:165-173 (1992).
Dorman et al., Characterization of Porin and ompR Mutants of a Virulent Strain of *Salmonella typhimurium*: ompR Mutants are Attenuated in Vivo, *Infect. Immun.* 57:2136-2140 (1989).
Dougan et al., Live Oral *Salmonella* Vaccines: Potential Use of Attenuated Strains as Carriers of Heterologous Antigens to the Immune System, *Parasite Immun.* 9:151-160 (1987).
Dul et al., Genetic Mapping of a Mutant Defective in D. L-Alanine Racemase in *Bacillus subtillis* 168, *J. Bacteriol.* 115:1212 (1973).
Ferrari et al., Isolation of an Alanine Racemase Gene from *Bacillus subtillis* and its use for Plasmid Wraintenance In *B. subtillis*, *Bio/Technology* 3:1003-1007 (1985.
Gait, ed., Oligonucleotide Synthesis, A Practical Approach (1984).
Galan and Curtiss, Virulence and Vaccine Potential of phoP Mutants of *Salmonella typhimurium*, *Microb. Pathogen* 6:433-443 (1989).
Gentschey et al., *Salmonella* Strain Secreting Active Listeriolysin Changes Its Intracellular Localization, *Infect. Imm.* 63(10):4202-4205 (1995).
Gerdes et al., Unique Type of Plasmid Maintenance Function: Postsegregational Killing of Plasmid-Free Cells, *Proc. Natl. Acad. Sci. USA* 83:3116-3120 (1986).
Gerdes et al., Mechanism of Postsegregational Killing by the *hok* Gene Product of the *par*B System of Plasmid R1 and its Homology with the *re/F* Gene Product of the *E. coli re/B* Operon, *EMBO Journal* 5(8):2023-2029 (1986).
Gerdes et al., The *hok* Killer Gene Family in Gram-Negative Bacteria, *New Biol.* 2946-956 (1990).
Germanier and Furer, Immunity in Experimental Salmonelosis, *Infect. Immun.* 4:663-673 (1971).

Germanier and Furer, Isolation and Characterization of Gal E. Mutant Ty. 21a of *Salmonella typhi*: A Candidate Strain for a Live, Oral Typhoid Vaccine, *J. Infec. Dis.* 131:553-558 (1975).

Giladi et al., Integration Host Factor Stimulates the Phage Lambda pL Promoter, *J. Mol. Biol.* 231:109-121 (1990).

Glover, ed., DNA Cloning, A Practical Approach, vols. IU and II (1985).

Guzman et al., Tight Regulation, Modulation, and High-Level Expression by vectors Containing the Arabinose PBAD Promoter, *J. Bacteriol.* 177(14):4121-4130 (1995).

Hames and Higgins, eds., Nucleic Acid Hybridization, A Practical Approach (1984).

Hecker et al., Role of relA Mutation in the Survival of Amino Acid-Starved *Escherichia coli*, *Arch Microbiol.* 143:400-402 (1986).

Helander et al., Preferential Synthesis of Heptaacyl Lipopolysaccharide by the *ssc* Permeability Mutant of *Salmonella typhimurium*, *Eur. J. Biochem.*, 204:1101-1106 (1992).

Hess et al., Superior Efficacy of Secreted Over Somatic Antigen Display in Recombinant *Salmonella* Vaccine Induced Protection Against Listeriosis, *Proc. natl. Acad. Sci. USA* 93:1458-1463 (1996).

Hirvas et al., Identification and Sequence Analysis of the Gene Mutated in the Conditionally Lethal Outer Membrane Permeability Mutant SS-C of *Salmonella typhimurium*, *EMBO j.*, 10(4):1017-1023 (1991).

Hoe et al., Temperature Sensing in *Yersinia pestis*:Regulation of *yopE* Transcription by *lcrF*, *J. Bacteriol.* 174:4275-4286 (1992).

Hone et al., A *galE via* (vi Antigen-Negative) Mutant of *Salmonella typhi* Ty2 Retains Virulence in Humans, Infect. Immun. 56:1326-1333 (1988).

Hromockyi et al., Temperature Regulation of Shigella Virulence: Identification of the Repressor Gene virR, An Analogue of hns, and Partial Complementation by Tyrosyl Transfer RNA (tRNA 1Tyr), *Mol. Micro.* 6:2113-2124 (1991).

Jaqusztyn-Krynicka et al., Expression of *Streptococcus* mutans Aspartate-Semialdehyde Dehydrogenase Gene Cloned Into Plasmid pBR322, *J. Gen. Microbiol.* 128:1135-1145 (1982).

Johnson et al., The Role of a Stress-Response Protein in *Salmonella typhimurium* Virulence, *Mol. Microbiol.* 5:401-407 (1991).

Jones et al., Induction of Proteins in Response to Low Temperature in *Escherichia coli*, *J. Bacteriol.* 169:2092-2095 (1987).

Kaniga et al., A Wide-Host Suicide Vector for Improving Reverse Genetics in Gram-Negative Bacteria: Inactivation of the *bla*A Gene of *Yersinia enterocloitica*, *Gene* 109:137-141 (1991).

Kelly et al., Characterization and Protective Properties of Attenuated Mutants of *Salmonella choleraesus*, Infect. Immun. 60:4881-4890 (1992).

Knudsen and Karlström, Development of Efficient Suicide Mechanisms for Biological Containment of Bacteria, Applied and Environmental Microbiology 57(1):85-92 (1991).

Kushner, Construction of Versatile Low-Copy-Number Vectors for Cloning, Sequencing and Gene Expression in *Escherichia coli*, *Gene* 100:195-199 (1990).

Lambert de Rouvroit et al., Role of the Transcriptional Activator, VirF. and Temperature in the Expression of pYV Plasmid Genes of *Yersinia enterocloitica*, *Molec. Microbiol.* 6:395-409 (1992).

Lieb, Studies of Heat-Inducible Lambda Bacteriophage, *J. Mol. Biol.* 16:149-163 (1966).

Lugtenberg et al., Temperature-Sensitive Mutant of *Escherichia coli* K-12 with an Impaired D-Alanine: D-Alanine Ligase, *J. Bacteriol.* 113:96-104 (1973).

McGhee and Mestecky, The Secretory Immune System, *Ann. N. Y. Acad. Sci.*, vol. 409 (1983).

Miller, Experiments in Molecular Genetics (Cold Spring Harbor laboratory, 1972).

Miller et al., A Two-Component Regulatory System (phoP phoQ) Controls *Salmonella typhimurium* Virulence, *Proc. Natl. Acad. Sci. USA* 86:5054-5058 (1989).

Miller and Mekalanos, A Novel Suicide Vector and Its Use in Construction of Insertion Mutations: Osmoregulation of Outer Membrane Proteins and Virulence Determinants in *Vibrio choleae* Requires *tox*R, *J. Bacteriol.* 170:2575-2583 (1988).

Miller, A Short Course in Bacterial Genetics (Cold Spring Harbor Laboratory, 1992).

Miyakawa et al., Cell Wall Peptidoglycan Mutants of *Escherichia coli* K-12: Existence of Two Clusters of Genes, *mra* And *mrb*. For Cell Wall Peptidoglycan Biosynthesis, *J. Bacteriol.* 112:950 (1972).

Molin et al., Suicidal Genetic Elements and their use in Biological Containment of Bacteria, Annual Review of Microbiology 47:139-166 (1993).

Molin et al., Release of Engineered Microorganisms: Biological Containment and Improved Predictability for Risk Assessment, *AMBIO 22(4)*:242-245 (1993).

Molin et al., Conditional suicide system for containment of bacteria and plasmids, *Bio/Technology* 5:1315-1318 (1987).

Munthali et al., Use of Colicin E3 for Biological Containment of Microorganisms, *App. Environ. Microbiol.* 62(5):1805-1807 (1996).

Munthali et al., *Bio/Technology* 14(2):189-191 (1996).

Neidhardt et al., The genetics and Regulation of Heat-Shock Proteins, *Annu. Rev. Genet.* 18:295-329 (1984).

Nvström, Role of Guanosine Tetraphophate in Gene Expression and the Survival of Glucose of Seryl-tRNA Starved Cells of *Escherichia coli* K12, *Mol. Gen. Genet.* 245:355-362 (1994).

O'Brien, ed., Genetic Maps (Cold Spring Harbor Laboratory, 1987).

O'Connor et al., Highly Repressible Expression System for Cloning Genes that Specify Potentially Toxic Proteins, *J. Bacteriol.* 169:4457-4462 (1987).

Orga et al., Handbook of Mucosal Immunology (Academic Press, San Diego, CA 1994).

Perbal, A Practical Guide to Molecular Cloning, A Wiley-Interscience Publication (1984).

Poteete et al., Operator Sequences of Bacteriophages P22 and 21, *J. Mol. Biol.* 137:81-91 (1980).

Poulsen et al., The gef Gene from *Escherichia coli* is Regulated at the Level of Translation, *Mol. Microbiol.* 5:1639-1648 (1991).

Ooronfleh et al., Identification and Characterization of Novel Low-Temperature-Inducible Promoters of *Escherichia coli*, *J. Bacteriol.* 174:7902-7909 (1992).

Ramos et al., Suicide Microbes on the Loose, *Bio/Technology* 13:35-37 (1995).

Reader et al., Lysis Defective Mutants of Bacteriophage Lambda: On the Role of the S Function in Lysis, *Virology* 43:623-637 (1971).

Reddy et al., Hyperexpression and Purification of *Escherichia coli* Advenviate Cyclase Using a Vector Designed for Expression of lethal Gene Products, *Nucleo. Res.* 17(24):10473-10489 (1989).

Remaut et al., Plasmid Vectors for High-Efficiency Expression Controlled by the pL Promoter of Coliphage Lambda, *Gene* 15:81-93 (1981).

Remaut et al., Improved Plasmid Vectors with a Thermoinducible Expression and Temperature-Regulated Runaway Replication, *Gene* 22:103-113 (1983).

Rennell and Poteete, Phage P22 Lysis Genes: Nucleotide Sequences and Functional Relationships with T4 and $\lambda$ Genes, *Virology* 143:280-289 (1985).

Sambrook et al., Molecular Cloning: A Laboratory Manual (Cold Spring Harbor Laboratory, 1989).

Sander et al., Nucleotide Sequence of Bacteriophage $\lambda$, DNA, J. Mol. Biol. 162:729-773 (1982).

Sauer et al., Primary Structure of the Phage P22 Repressor and its Gene c2, *Biochem.* 20:3591-3598 (1981).

Schödel, Oral Vaccination Using Recombinant Bacteria, *Semin. Immunol.* 2:341-349 (1990).

Schödel, Recombinant Avirulent Salmonellae as Oral Vaccine Carriers, *Infection 20(1)*:1-8 (1992).

Schweder et al,, *App. Microbiol. Biotechnol.* 38(1):91-93 (1992).

Schweder et al., *Escherichia coli* K12 relA Strains as Safe Hosts for Expression of Recombinant DNA, *Appl. Microbiol. Biotechnol.* 42:718-723 (1995).

Sigwart et al., Effect of a purA Mutation on Efficacy of *Salmonella* Live-Vaccine Vectors, *Infection and Immunity 57(6)*:1858-1861 (1989).

Sites et al., Basic and Clinical Immunology (Lange Medical Books, Los Altos, CA 1994).

Sizemore et al., Attenuated Shigella as a DNA Delivery Vehicle for DNA-Mediated Immunization, *Science* 270:299-302 (1995).

Spector et al., Starvation-Inducible loci of *Salmonella typhimurium*:Regulation and Roles in Starvation-Survival, *Mol. Micro.* 6:1467-1476 (1992).

Studier et al., Gene Expression Technology, *Methods Enzymol.* 185:60-89 (1990).

Tacket et al., Comparison of the Safety and Immunogenicity of a Δcya Δcrp *Salmonella typhi* Strains in Adult volunteers, *Infect. Immun.* 60:536-541 (1992).

Tanabe et al., Identification of the Pr9moter Region of the *Escherichia coli* Major Cold Shock Gene, *cspA, J. Bacteriol.* 174:3867-3873 (1992).

Tao et al., Sequence and Characterization of pvullR, the PvuII Endonuclease Gene, and of puvIIC, Is Regulatory Gene, *J. Bacteriol.* 174(10):3395-3398 (1992).

Temple et al., Survival of Two Enterobacteria in Feces Buried in Soil Under Field Conditions, *Appl. Environ. Microbiol.* 40:794-797 (1980).

Umbarger, Amino Acid Biosynthesis and its Regulation, *Ann. Rev. Biochem:* 47:533 (1978).

Vasina et al., Recombinant Protein Expression at Low Temperatures Under the transcriptional Control of the Major *Escherichia coli* Cold Shock Promoter *cspA, Appl. Environ. Micro.* 62(4):1444-1447 (1996).

Vazquez et al., *FEMS Microbiol. Lett. 121*:11-18 (1994).

Vuorio et al., Mutants Carrying Conditionally Lethal Mutations in outer Membrane Genes *omsA* and *firA* (ssc) are Phenotypically Similar, and *omsA* is Allelic to Vica., *J. Bacterio. 174(22)*:7090-7097 (1992).

Wüsman, The characterization of an Alanine Racemase Mutant of *Escherichia coli, Genet. Res. Comb.* 20:269-277 (1972).

Wüsman, A Genetic Map of Several Mutations Affecting the Mucopeptide Laver of *Echerichia coli, Genet. Res. Comb.* 20:65-74 (1972).

Yarrington et al., Dual-Origin Plasmid Vectors Whose Origin of Replication is Controlled by the Coliphage Lambda Promoters PL, *Gene* 28:293-300 (1984).

Young, Bacteriophage Lysis: Mechanism and Regulation, *Microbiol. Rev.* 56:430-481 (1992).

Krogh et al., J. Bacteriol., vol. 180, *Lysis genes of the Bacillus substilis defective prophage PBSX,* pp. 2110, 2117, Apr. 1998.

Young and Blasi, FEMS Microbiol. Rev., vol. 17, *Holins: form and function in bacteriophage lysis,* (abstract) Aug. 1995.

* cited by examiner

A *pir* -dependent suicide vector

A *pir*-dependent suicide construct for insertion of the $P_R$ driven c2 gene and *cI857* repressor into the *S. typhimurium asd* gene on the chromosome.

Figure 4
The Environmentally Limited Viability Components in the *S. typhimurium* Strain MGN-417

The ELVS expression vector intermediate.

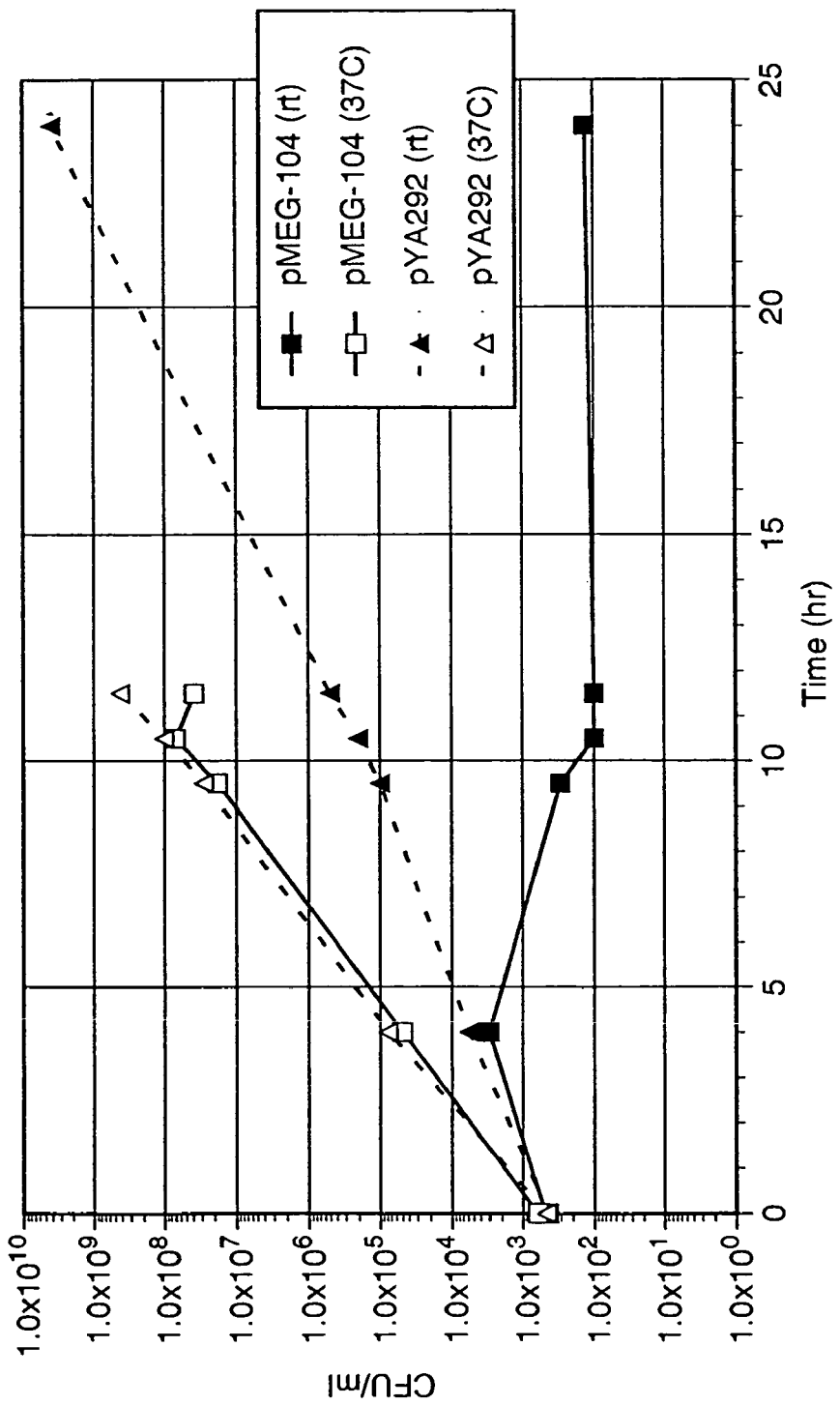

US 7,871,604 B1

RECOMBINANT BACTERIAL VACCINE SYSTEM WITH ENVIRONMENTALLY LIMITED VIABILITY

This application is a continuation of copending application Ser. No. 08/473,789, filed Jun. 7, 1995, entitled "RECOMBINANT BACTERIAL VACCINE SYSTEM WITH ENVIRONMENTALLY LIMITED VIABILITY," by Roy Curtiss, III and Steve A. Tinge. Application Ser. No. 08/473,789, filed Jun. 7, 1995, is hereby incorporated herein by reference.

The United States Government has rights to this invention pursuant to PHS Grants DE06669, AI24533, and HD29099.

BACKGROUND OF THE INVENTION

The invention relates to recombinant microorganisms with environmentally limited growth and viability, and more particularly to recombinant microorganisms that will not grow outside of a host organism.

Genetically engineered microorganisms have widespread utility and importance. For example, they can be used to produce foreign proteins, and thus can be used industrially for synthesis of products such as interferons, insulin, and growth hormone; they can also be used as vaccines to produce an immune response. However, it is undesirable for the genetically-engineered microorganism to persist in the environment.

Physical containment was the first means used to control the spread of genetically engineered microorganisms. More sophisticated means were then developed where microorganisms were contained by introducing debilitative mutations that prevent their growth in the absence of specific growth conditions, such as a particular amino acid. U.S. Pat. No. 4,190,495 discloses microorganisms with multiple mutations to prevent growth or genetic transfer outside of the controlled laboratory conditions.

Suicide plasmids have been described for use in biological containment of microorganisms (Molin et al., *Annual Review of Microbiology* 47:139-166 (1993)). Suicide plasmids generally use differential expression of a specific gene in and out of a controlled environment to prevent survival of the microorganism outside of the controlled environment. The use of suicide plasmids or systems has been limited to the repression of a required gene, or the repression of a lethal gene, under laboratory or other artificial conditions. In the absence of the supplied stimulus, the lethal gene becomes expressed. Either event leads to cell death either, directly or due to a severe competitive disadvantage. Most suicide systems depend upon expression of a gene that is actively toxic to the microorganism. A common problem with active suicide systems is the high selective pressure for mutations in the killing gene. This is analyzed, for example, by Knudsen and Karlström, *Applied and Environmental Microbiology* 57(1):85-92 (1991), who used a suicide function controlled by LacI$^q$ binding to Plac to repress expression of relF, thus preventing the suicide that would be caused by synthesis of the relF gene product. Expression of RelF, and thus display of the suicide phenotype, required the addition of IPTG. This system therefore served as a laboratory model to study induction of host killing within the plasmid-containing host or after transfer of the plasmid to a host lacking the LacI encoded repressor. The efficacy of the system was limited on the one hand by mutations that made killing by the relF gene product ineffective, and on the other hand by low level expression of relF even in the absence of added IPTG such that cells in the culture grew slowly.

Molin et al., *Bio/Technology* 5:1315-1318 (1987), describes the use of hok, encoding a small peptide that is lethal when expressed in many bacterial species, to prevent survival of a recombinant microorganism when outside of a controlled fermenter environment. The hok gene is homologous to the relF gene. Molin et al. (1987) uses an invertible promoter to control expression of hok. Stochastic inversion of the inactive promoter to the active orientation causes the bacterial population to dwindle due to the death of a predetermined fraction of the cells per unit time. This stochastic cell death is dependent on the relative expression of the fimB and fimE genes which control the flip-flop orientation of the invertable promoter. This system does not lead to a rapid drop in bacterial population density except under ideal laboratory conditions.

Molin and Kjelleberg, *AMBIO* 22(4):242-245 (1993), and Ramos et al., *Bio/Technology* 13:35-37 (1995) have hypothesized that microorganisms for release in natural environments might be regulated by suicide genes. Molin and Kjelleberg describe the use of a suicide gene regulated by general or specific starvation. Ramos et al. disclose the use of gef family genes, of which hok and relF are members, and nuclease genes, as suicide genes. Ramos et al. also described killing by these gene products expressed upon IPTG induction of the inducible Plac fused to the gef gene. Ramos et al. describe regulation of the suicide function by loss of a specific nutrient or condition, such as occurs outside of artificially controlled conditions, and by linking the regulatory stimulus to the task of the microorganism. This was accomplished by controlling the rate of inversion of a promoter which in one orientation causes expression of relF, resulting in cell death. This system, of course, only leads to a gradual loss in the viability of the cell population once the cells are in an environment lacking a nutrient. Ramos et al. also suggests the use of biological containment to make live vaccines feasible. However, Ramos et al. (page 37) points out that the complexity of the human gut precludes the design of control circuits based on specific stimuli, suggesting containment based on differential growth rates in and out of the gut. Ramos et al. does not suggest any regulatory system that could achieve this goal.

Live bacterial vaccines have been described that express a desired antigen and colonize the intestinal tract of animals (Curtiss et al., *Curr. Topics Micro. Immun.* 146:35-49 (1989); Curtiss, *Attenuated Salmonella Strains as Live Vectors for the Expression of Foreign Antigens*, in *New Generation Vaccines* (Woodrow and Levine, eds., Marcel Dekker, New York, 1990) pages 161-188; Schödel, *Infection* 20(1):1-8 (1992); Cárdenas and Clements, *Clinical Micro. Rev.* 5(3):328-342 (1992)). Most work to date has used avirulent *Salmonella typhimurium* strains synthesizing various foreign antigens for immunization of mice, chickens and pigs. Several avirulent *S. typhi* vectors have been evaluated in human volunteers (Tacket et al., *Infect. Immun.* 60:536-541 (1992)) and several phase I clinical trials with recombinant avirulent *S. typhi* strains are in progress in the U.S. and Europe.

Although research progress toward expanding and further improving the recombinant avirulent *Salmonella* antigen delivery strategy has progressed at a reasonable rate, commercial development of recombinant vaccines for the control of infectious diseases of animals or humans has been slow. An important safety advantage of the live attenuated bacterial vaccine vectors as compared to the use of viral vector based vaccines is the ability to treat an immunized patient with oral ciprofloxacin or amoxicillin, should an adverse reaction occur. However, current live bacterial vaccines have the disadvantage that oral administration leads to fecal shedding, with the potential risk that the bacterial vaccine strain will proliferate in nature and infect individuals not selected for immunization. It is known, for example, that fecal coliforms can persist for extended periods under field conditions, with only moderate reductions in numbers (Temple et al., *Appl. Environ. Microbiol.* 40:794-797 (1980)). There is also concern that these surviving vaccine strains will transmit their cloned genetic information to more robust microorganisms encountered in nature with not always predictable consequences. Although the transmission of most expressed genes to wild-type microbial species would not be harmful, some recombinant vectors expressing genes for sperm-specific antigens or lymphokines could have adverse consequences if widely disseminated. It is therefore desirable to have a biological containment system regulated by the conditions that differ between the target environment and other environments. In the case of live recombinant vaccines, it is desirable to have a microorganism that survives inside the animal, but dies outside of the animal. Live attenuated bacterial antigen delivery vectors with inherent biological containment features to preclude survival, proliferation and gene transfer in nature would increase the acceptability and enthusiasm for use of this type of vaccine delivery system.

It is therefore an object of the present invention to provide an Environmentally Limited Viability System for use in controlling viability of targeted microorganisms and limiting the survival of recombinant extrachromosomal genetic information if transferred to other microorganisms.

It is another object of the invention to provide a live recombinant vaccine with environmentally limited viability.

It is a further object of the invention to provide a method of vaccination using a live recombinant vaccine with environmentally limited viability.

SUMMARY OF THE INVENTION

Disclosed is an Environmentally Limited Viability System (ELVS) for microorganisms based on differences between permissive and non-permissive environments. Viability of the microorganisms are limited to the permissive environment by specifically expressing one or more essential genes only in the permissive environment, and/or expression of one or more lethal genes only in the non-permissive environment. Environmentally Limited Viability Systems are also disclosed involving coordinate expression of a combination of required genes and lethal genes. Microorganisms containing an Environmentally Limited Viability System are useful for release into a permissive environment. Temperature regulated Environmentally Limited Viability Systems are particularly suited for use with recombinant avirulent *Salmonella* vaccines for warm-blooded animals by limiting the vaccine growth to the warmer environment inside the animal. Such vaccines can be administered to immunize humans or warm-blooded animals against bacterial, viral, mycotic and parasitic pathogens, especially those that colonize on or invade through mucosal surfaces. This antigen delivery system can also be used for expression of gamete-specific antigens to induce immune responses to block fertilization, or to induce immune responses to tumor antigens.

A preferred example of a temperature regulated Environmentally Limited Viability System is disclosed. An expression vector containing the essential *S. typhimurium* asd gene, operatively linked to the bacteriophage lambda promoter left ($\lambda P_L$), and the lethal lysis genes lys13 and lys19 of bacteriophage P22, operatively linked to the bacteriophage P22 promoter right ($P22P_R$), is placed in a bacterial cell having a defined deletion of the *S. typhimurium* asd gene containing an insertion of the bacteriophage P22 c2 repressor gene operatively linked to the bacteriophage lambda promoter right ($\lambda P_R$). The inserted cartridge also contains the temperature sensitive bacteriophage lambda repressor gene cI857 (cI857), responsible for the temperature-dependent regulation of $\lambda P_R$ and $\lambda P_L$. This use of lambda promoters allows expression of the gene products encoded by the genes fused to them at temperatures greater than about 30° C., especially at about 37° C., but increasingly represses expression, due to the cI857 repressor, at temperatures below about 30° C. This results in the expression of both the essential asd gene and the bacteriophage P22 c2 repressor at temperatures greater than about 30° C., especially at about 37° C. The bacteriophage P22 c2 repressor in turn prevents the expression of the lethal lysis genes at temperatures greater than about 30° C., especially at about 37° C. The inverse occurs at temperatures below about 30° C., with little or no expression of the asd gene and efficient expression of the P22 lysis genes due to derepression, both of which cause cell lysis and death if the cell attempts growth at temperatures below about 30° C., especially at about 25° C.

This Environmentally Limited Viability System can be reinforced by introducing a temperature-regulated chromosomal polA gene, which is expressed at temperatures greater than about 30° C., especially at about 37° C., but not at temperatures below about 30° C., especially at about 25° C. Since the expression vector containing the asd gene requires expression of the polA gene for replication, the expression vector containing the asd gene will not be able to replicate at temperatures below about 30° C., thus leading to loss of the vector and cell death.

BRIEF DESCRIPTION OF THE DRAWINGS

FIG. 4 is a diagram of a vector based Environmentally Limited Viability System (ELVS) with *S. typhimurium* host MGN-392 containing expression vector pMEG-104, the combination designated as strain MGN-417. pMEG-104 contains the asd gene of *S. typhimurium* operatively linked to the promoter left of bacteriophage lambda ($\lambda P_L$), and the lysis genes of bacteriophage P22 (lys13 and lys19) operatively linked to the promoter right of bacteriophage P22 ($P22.P_R$). The promoter left of bacteriophage lambda and promoter right of bacteriophage P22 are placed in opposite orientations on the vector such that transcription of the promoter left of bacteriophage lambda will produce an antisense RNA of the lysis genes and transcription of the promoter right of bacteriophage P22 will produce an antisense RNA of the asd gene. Both genes are in a cartridge flanked by two different transcription terminators (trpA term and 5S T1 T2). pMEG-104 also contains the low copy-number, DNA polymerase I-dependent p15A origin of replication (ori). The host cell MGN-392 contains the cI857 and c2 repressor gene cartridge derived from pMEG-096 on its chromosome. This cartridge replaces a central portion of the chromosomal asd gene of the host cell. This cartridge provides thermally regulated limited viability when the plasmid pMEG-104 is present in this host cell. Bold arrows depict temperature-regulated expression of the vector components of the ELVS.

FIG. 6 is a graph of the growth (CFU/ml) versus time (hours) of *S. typhimurium* hosts with and without an Environmentally Limited Viability System. Filled squares indicate growth points of cells containing pMEG-104 grown at room temperature. Open squares indicate growth points of cells containing pMEG-104 grown at 37° C. Filled triangles indicate growth points of cells containing the Asd$^+$ vector pYA292 grown at room temperature. Open triangles indicate growth points of cells containing pYA292 grown at 37° C.

DETAILED DESCRIPTION OF THE INVENTION

Figure 1:
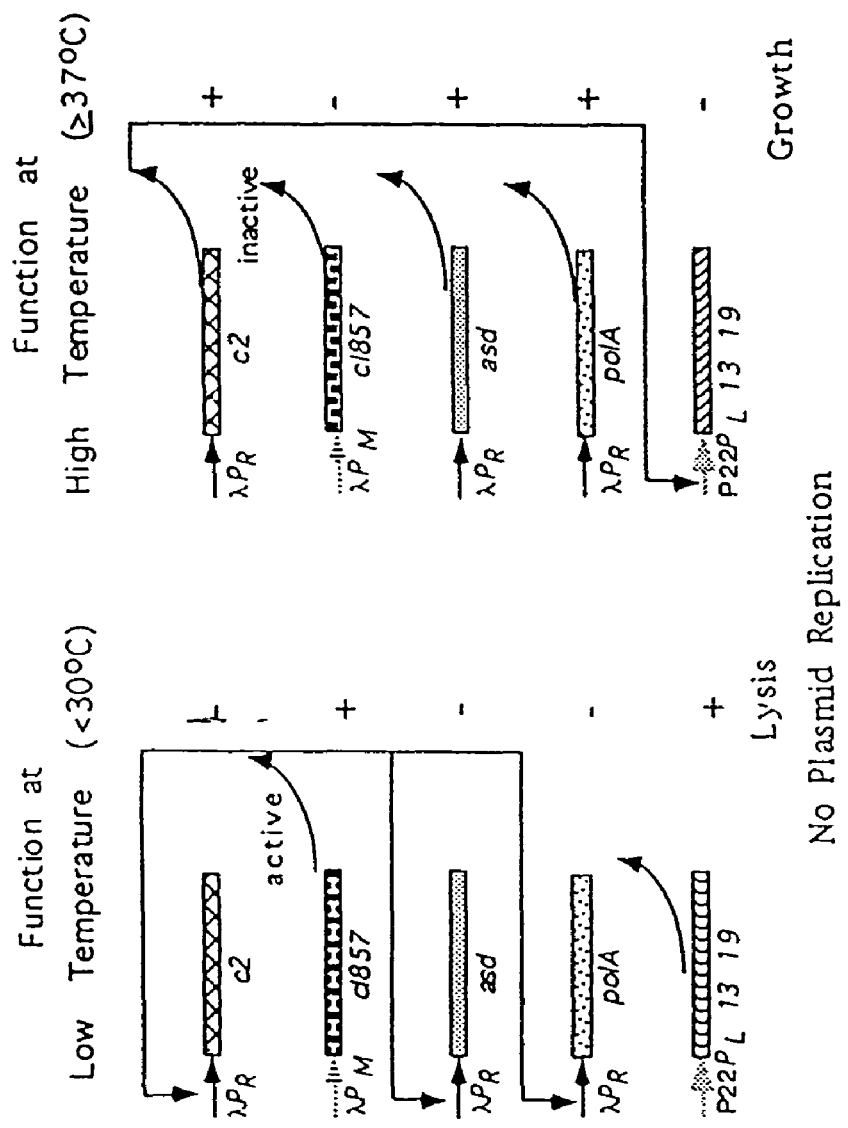
FIG. 1 is a diagram of an Environmentally Limited Viability System including a plasmid and chromosomal components, using a temperature-regulated asd gene on a PolA-dependent plasmid. The arrows illustrate the interaction of the repressors and promoter/operator regions for lambda and P22 at low and high temperatures, while the +/− indicates the production of a functional gene product. The promoters and regulators depicted may be interchanged with other environmentally regulated systems as they are characterized.

There are two main components required for a successful biological containment system. The first component consists of genes encoding products that are either essential or potentially fatal to the bacterial cells containing them. The second component is a regulatory system to turn the critical genes on or off at the appropriate time. The challenge presented by a containment system for a live bacterial vaccine is the recognition of an environmental trigger that will signal the death of the cell upon release into a non-permissive environment, but will not prevent growth in a permissive environment.

The disclosed Environmentally Limited Viability System combines specific regulation with essential and/or lethal genes to limit the viability of a microorganism to a permissive environment. The Environmentally Limited Viability System can be combined with other mutations to limit the virulence of the bacterial host. A containment system encoding both essential and lethal gene products requires the cell maintain the desired regulation or suffer either loss of an essential component or the effect of a lethal product. In the preferred embodiment, the essential gene and the lethal gene are extra-chromosomal, for example, on a plasmid. However, any or all of the components of the Environmentally Limited Viability System can be located on a chromosome of the host microorganism.

The Environmentally Limited Viability System makes use of genetically engineered host cells which can be maintained as a genetically stable population, wherein the host cells express a desired expression product. The host cells used for the Environmentally Limited Viability System contain environmentally regulated essential genes, lethal genes and/or replication genes. The expression of these genes is regulated to allow expression of the essential and replication genes only in a permissive environment, and expression of the lethal genes in non-permissive environments. Host cells used in the Environmentally Limited Viability System characteristically have an inactivated native gene encoding a gene essential for cell survival. A copy of this gene, which acts as an essential gene in the system, is placed on the vector of the system to provide selective pressure for maintenance of the vector.

The Environmentally Limited Viability System makes use of host cells adapted for use of the genetic components of the system. Vectors which are suitable for transforming the host cells, which contain the essential and lethal genes, and into which the gene encoding the desired polypeptide may be inserted, are also described. The disclosed Environmentally Limited Viability System is suitable for use for the production of desired polypeptides in industrial settings, for example, by growth in fermenters. For example, recombinant production of dangerous toxins can be performed with a reduced risk of escape by using an Environmentally Limited Viability System. Microorganisms incorporating the system may also be used as live vaccines.

Genetic regulatory systems suitable for use in the Environmentally Limited Viability System are those that modulate gene expression based on environmental conditions, such as temperature, osmolarity, pH, and oxygen availability. A basic motif of many of these regulatory systems is an environmentally based change in a trans regulatory element that alters its interaction with a control sequence of the regulated gene. Such systems can be adapted to regulate the genes of the Environmentally Limited Viability System based on environmental changes that define a permissive and non-permissive environment.

As used herein, permissive environment refers to an environment in which microorganisms incorporating an Environmentally Limited Viability System are viable. Such an environment might possess a key characteristic, such as a specific temperature, osmolarity, pH, or oxygen concentration. As used herein, a non-permissive environment refers to an environment in which microorganisms incorporating an Environmentally Limited Viability System are non-viable. As used herein, a non-viable cell or microorganism refers to a cell or microorganism that cannot grow. Viability is always considered relative to specific environments and environmental conditions. Thus, a cell is considered non-viable in a particular environment even though the cell would be viable in other environments.

A. Essential Genes

The Environmentally Limited Viability System makes use of essential genes to limit cell viability and to provide selective pressure for maintenance of the vector component of the system. An essential gene, as used herein, refers to a gene required for cell viability. Containment is provided by regulating the essential gene, such that the gene is expressed in a permissive environment but is not expressed in a non-permissive environment.

As used herein, "gene" refers to a nucleic acid sequence having a coding sequence operatively linked to a control sequence. "Coding sequence" refers to a nucleic acid sequence encoding RNA or protein. The RNA or protein encoded by a coding sequence is referred to as an expression product. A coding sequence can encode one or more expression products. "Control sequence" refers to DNA sequences which are necessary to effect the expression of coding sequences to which they are operatively linked. Generally such control sequences include a promoter and ribosome binding site. The term "control sequence" is intended to include, at a minimum, all components whose presence is necessary for expression, and may also include additional components whose presence is advantageous, for example, operators. "Operatively linked" refers to a juxtaposition wherein the components so described are in a relationship permitting them to function in their intended manner. A control sequence operatively linked to a coding sequence refers to a control sequence ligated in such a way that expression of the Coding sequence is achieved under conditions compatible with the control sequences.

The essential gene or genes can be located on an extrachromosomal vector or on a chromosome of the microorganism. Placing regulated essential genes on the chromosome provides stability for the genes and allows multiple essential genes to be combined in a single Environmentally Limited Viability System without increasing the size and complexity of the vector portion of the system. It is preferred, however, that at least one essential gene be expressed on the vector portion of the system in order to provide selection for plasmid maintenance.

The essential gene is also used to maintain the vector component of the Environmentally Limited Viability System in microorganisms of the system. This is important because most plasmids are maintained through the use of antibiotic selection and in many natural environments the use of antibiotics is unworkable or undesirable. Maintenance of plasmids in recombinant hosts when present in natural environments preferably use a different selection system. A preferred selection method involves a balanced-lethal host-vector system, where an essential gene is carried on a vector and the chromosomal gene is deleted, creating a balanced-lethal condition. The "lethal" deletion is balanced by the presence of the vector borne copy of the wild-type gene.

Genes essential for metabolism or growth. Most genes encoding enzymes involved in the metabolism or growth of a microorganism can be used as essential genes. All that is required is that the gene is regulated so that it is expressed only in a permissive environment. It is preferred that the essential gene be derived from a gene in the host microorganism. In many bacteria, expression of modification methylases are required to prevent endogenous restriction endonucleases from cleaving the host chromosome. Thus a modification methylase gene can also be used as the essential gene. Genes required for nucleic acid replication, such as genes encoding DNA ligase and gyrase, are essential for cell growth and can be used as the essential gene.

Genes essential for cell wall or cell membrane integrity. All bacteria have a peptidoglycan layer of the cell wall which imparts shape and rigidity. The peptidoglycan is made of a polymer of repeating muramic acid-N-acetylglucosamine and is cross-linked by short peptides. In all gram-negative bacteria and in *Mycobacterium* and in *Nocardia* species of Eubacteria, the peptide is composed of L-alanine, D-glutamic acid, meso-diaminopimelic acid (DAP), and D-alanine. In most gram-positive microorganisms the DAP is replaced by its decarboxylation product L-lysine.

Enzymes which catalyze the biosynthesis of the cell wall component and its precursors are known in the art. For example, in the synthesis of peptidoglycans, the enzyme may be one which catalyzes the insertion of the cross-linking peptide, for example, D-alanyl-D-alanine ligase, or of the synthesis of the carbohydrate polymer, or it may be an enzyme which catalyzes a step in the biosynthesis of a precursor, for example, diaminopimelic acid (DAP). For a review of the biosynthesis of this family of amino acids, see Umbarger (1978). Examples of genes encoding enzymes which catalyze steps in the biosynthesis of DAP are known in the art for a variety of organisms, see, for example, *Genetic Maps* (O'Brien, ed., Cold Spring Harbor Laboratory, 1987), and include, for example, in *S. typhimurium* the dapA and dapB genes and for example, *E. coli*, the dapA, dapB, dapC, dapD, and dapE genes. Another enzyme which is essential for DAP synthesis is β-aspartate semialdehyde dehydrogenase (Asd), which is encoded by the asd gene.

The use of asd in an unregulated balanced-lethal system is described by (Nakayama et al., *Bio/Technology* 6:693-697 (1988)). This system uses plasmid vectors with the wild-type gene encoding the enzyme β-aspartate semialdehyde dehydrogenase required for the synthesis of DAP in conjunction with a *Salmonella* strain which has a chromosomal asd mutation. Since DAP is synthesized only by bacteria and is not present in the tissues of an immunized host, loss of the Asd$^+$ vector from the recombinant avirulent *Salmonella* leads to death and lysis of the bacterial cell (Nakayama et al. (1988)). In the disclosed Environmentally Limited Viability System, the asd balanced-lethal system can be adapted by regulating the expression of the essential asd gene.

Accordingly, a preferred essential gene is asd, encoding β-aspartate semialdehyde dehydrogenase, an enzyme required for the synthesis of an essential component of the rigid layer of the bacterial cell wall, namely diaminopimelic acid (DAP). DAP is only synthesized by bacteria and is not prevalent in the environment. DAP is synthesized in six enzymatic steps from β-aspartate semialdehyde, which, in turn, is synthesized in two steps from L-aspartic acid. In the first step, L-aspartic acid is phosphorylated by one of several (usually three) β-aspartokinases which are encoded by several (usually three) separate genes regulated independently by repression and/or feedback inhibition of the gene products by the ultimate end products L-threonine, L-methionine, and L-lysine. β-aspartophosphate is converted in one step to β-aspartic semialdehyde by β-aspartic semialdehyde dehydrogenase, the product of the asd gene. Mutants with a point mutation in or deletion of the asd gene as well as mutants with mutations in any of the six genes specifying the enzymes for converting β-aspartate semialdehyde to DAP have an obligatory requirement for DAP in all media. When DAP-requiring mutants are deprived of DAP, they die and are lysed, releasing their contents.

The gene for β-aspartate semialdehyde dehydrogenase from *Streptococcus mutans* PS 14 (UAB62) has been cloned and expressed in asd mutants of *E. coli*, as described by Jagusztyn-Krynicka, et al. (1982), and Curtiss et al. (1982). Subsequently, the *S. mutans* asd gene was sequenced by Cardineau and Curtiss (1987).

In both gram-positive and gram-negative bacteria, the peptide cross-linking repeating muramic acid-N-acetylglucosamine polymers contain D-alanine. D-alanine is synthesized from L-alanine by alanine racemase, the product of the dal gene (*B. subtilis*), and then is converted to a D-alanyl-D-alanine dipeptide by the enzyme D-alanyl-D-alanine ligase, the product of the ddI gene. D-alanine is coupled to the L-alanyl D-glutamyl DAP or L-alanyl-D-glutamyl-L lysine tripeptide which is attached to one muramic acid-N-acetylglucosamine polymer to form a pentapeptide. The terminal D-alanine is then cleaved during the enzymatic cross-linking reaction to the next muramic acid-N-acetylglucosamine polymer. Mutants of *Bacillus subtilis* lacking the ability to synthesize D-alanine or to synthesize D-alanyl-D-alanine lyse in media devoid of D-alanine or of the dipeptide. dal mutants of *B. subtilis* lacking alanine racemase have been isolated (Ferrari et al., *Bio/Technology* 3:1003-1007 (1985); Dul et al. (1973)). ddl mutants lacking D-alanyl D-alanine ligase have been isolated in *E. coli* (Wijsman (1972), Miyakawa et al.

(1972), Lugtenberg et al. (1973)) and in *B. subtilis*. As in the case of the asd and dap mutations, the inclusion of dal and/or ddI mutations in strains of bacteria limits the viability of the organisms, since such mutant strains are unable to survive in environments other than a carefully controlled laboratory environment.

All microorganisms have a cell membrane that retains the cytoplasmic contents. During growth, new membrane components must be synthesized to maintain the integrity of increased surface area of the membrane on the growing cell. Critical genes involved in metabolism of cell membrane components can be used for the essential gene. Such genes include genes involved in fatty acid biosynthesis (fab), fatty acid degradation (fad), phospholipid synthesis (pls), and phospholipases.

B. Lethal Genes

Regulated lethal genes are used in the Environmentally Limited Viability System to actively kill host cells that escape to a non-permissive environment. A lethal gene, as used herein, refers to a gene that is lethal to the host microorganism when expressed in the host. A regulated lethal gene which is repressed in the permissive environment, but expressed in the non-permissive environment, acts as a positive containment mechanism for the Environmentally Limited Viability System.

Lethal genes useful in the Environmentally Limited Viability System include cell-killing gene products of the gef gene family that form holes in cell membranes when over-produced. Some of these host killing genes, such as hok, are plasmid derived and ensure that plasmid-free cells do not survive (Gerdes et al., *Proc. Natl. Acad. Sci*, USA 83:3116-3120 (1986)). Others, such as gef and relF, are of chromosomal origin with unclear functions (Poulsen et al., *Mol. Microbiol.* 5:1639-1648 (1991), Gerdes et al., *EMBO J.* 5:2023-2029 (1986), Gerdes et al., *New Biol.* 2:946-956 (1990)). Other bacterial host killing gene products useful as lethal genes include nucleases (Molin et al., *Annu. Rev. Microbiol.* 47:139-166 (1983)), phospholipases (Givskov et al., *J. Bacteriol.* 170:5855-5862 (1988)) and plasmid maintenance genes (Figurski et al. (1982)). Endolysins and holins of the bacteriophages lambda (Bienkowska-Szewczyk et al., *Mol. Gen. Genet.* 184:111-114 (1981), Reader and Siminovitch, *Virology* 43:623-637 (1971)) and P22 (Rennell and Poteete, *Virology* 143:280-289 (1985)) are also available. Their expression forms lesions in the bacterial inner membrane with subsequent degradation of the cell wall and release of cytoplasmic contents (Young, *Microbiol. Rev.* 56:430-481 (1992)). Preferred lethal genes are the combination of bacteriophage P22 lysis genes 13 and 19, coding for a porin and lysozyme, respectively. The joint action of these two proteins leads to production of holes in the cell membrane and degradation of the bacterial cell wall. In adapting the Environmentally Limited Viability System to various host cells; it is preferred that lysis genes from phage that normally infect the chosen host be used as the lethal genes.

A gene encoding a tRNA (including a suppressor tRNA), or a tRNA that would have acceptor activity but a wrong codon to cause synthesis of mutant proteins, could also be used as a lethal gene. A nuclease active against DNA or mRNA could also be lethal when overexpressed.

The lethal gene may be located on a chromosome of the host microorganism or an extrachromosomal element. It is preferred that lethal genes used in the Environmentally Limited Viability System be expressed on a vector. One advantage is to limit the amount of growth during which an inactivating mutation could occur.

It is preferred that the lethal gene be placed on an extrachromosomal vector regulated by a chromosomally expressed negative trans regulatory element. With this arrangement, should the plasmid be transferred to another microorganism, the lethal gene will be expressed constitutively and lead to the demise of that recipient cell. Thus, the Environmentally Limited Viability System will prevent both survival and spread of the recombinant strain within the environment and transmission of recombinant plasmids within natural populations of bacteria.

C. Replication Genes

Biological containment of the Environmentally Limited Viability System can be enhanced by regulating the expression of a replication gene. A replication gene, as used herein, refers to a gene required for replication of an extrachromosomal vector. Use of a properly regulated replication gene reinforces the dependence of the cell on an essential gene by placing the vector containing the essential gene into a host with a gene required for the replication and maintenance of that vector. A preferred replication gene is polA, encoding DNA polymerase I, an enzyme required for replication of a number of plasmid replicons. The failure of the host cell to synthesize. DNA polymerase I will halt plasmid vector replication and progeny cells will be formed lacking the plasmid containing the essential gene, thus resulting in non-viable cells (Kingsbury et al., *J. Bacteriol.* 114:1116-1124 (1973)).

It is preferred that the environmentally regulated replication gene be placed on a chromosome of the host microorganism.

D. Regulatory Elements

The three categories of genes described above (essential, lethal, and replication) require a regulatory system that ensures viability in the permissive environment and rapid death and lysis in the non-permissive environment. Regulation is coordinated and maintained using control sequences either directly linked to the essential, lethal, and replication genes of the Environmentally Limited Viability System, or linked to coding sequences encoding trans regulatory elements that modulate the expression of the genes of the Environmentally Limited Viability System. The switch in expression is mediated by environmentally based changes in trans regulatory elements. In general, the genes of the Environmentally Limited Viability System can be regulated 1) by linking the coding sequences to control sequences that promote or prevent transcription in the permissive and non-permissive environments, 2) by regulating the expression of trans regulatory elements that in turn promote or prevent transcription of the genes of the Environmentally Limited Viability System, 3) by adapting or altering trans regulatory elements, which act on the genes of the Environmentally Limited Viability System, to be active or inactive in either the permissive or non-permissive environment, or using combinations of these schemes. The Environmentally Limited Viability System requires the use of various promoters to coordinate expression of different elements of the system. Some elements, such as temperature-sensitive repressors or environment-specific regulatory elements, use constitutive promoters.

1. Trans Regulatory Elements. As used herein, trans regulatory, element refers to a molecule or complex that modulates the expression of a gene. Examples include repressors that bind to operators in a control sequence, and antisense RNA that binds to and prevents translation of a mRNA. For use in Environmentally Limited Viability Systems, expression from regulated promoters is modulated by promoter regulatory proteins. These promoter regulatory proteins can function to induce or repress transcription from the promoter.

Another type of trans regulatory element is RNA polymerase. Genes of the Environmentally Limited Viability System can be regulated by linking them to promoters recognized only by specific RNA polymerases. By regulating the expression of the specific RNA polymerase, expression of the gene is also regulated. For example, T7 RNA polymerase requires a specific promoter sequence that is not recognized by bacterial RNA polymerases. A T7 RNA polymerase gene can be placed in the host cell, regulated to be expressed only in the permissive or non-permissive environment. Expression of the T7 RNA polymerase will in turn express any gene linked to a T7 RNA polymerase promoter. A description of how to use T7 RNA polymerase to regulate expression of a gene of interest, including descriptions of nucleic acid sequences useful for this regulation appears in Studier et al., Methods Enzymol. 185:60-89 (1990).

Another type of trans regulatory element is antisense RNA. Antisense RNA is complementary to a nucleic acid sequence of a gene to be regulated. Hybridization between the antisense RNA and the target sequence prevent expression of the gene. Typically, antisense RNA complementary to the mRNA of a gene is used. Expression of the genes of the Environmentally Limited Viability System is regulated by controlling the expression of the antisense RNA. Expression of the antisense RNA in turn prevents expression of the gene of interest. A complete description of how to use antisense RNA to regulate expression of a gene of interest appears in U.S. Pat. No. 5,190,931.

Trans regulatory elements, such as repressors or antisense RNA, can be expressed from either the chromosome or a plasmid. To limit the size and complexity of the plasmid portion of the system, however, it is preferred that these regulatory elements be expressed from the bacterial chromosome.

2. Temperature Sensitive Regulation. A preferred type of regulation for microorganisms intended for growth in humans or warm-blooded animals is temperature regulation. This is based on the contrast between the high and constant body temperature present in mammals and birds and the low and variable temperature present in the ambient environment into which microorganisms are shed. To accomplish this, a preferred Environmentally Limited Viability System expresses genes ensuring survival at about 37° C. and prevents expression of genes that would cause death or lysis at about 37° C. The system is designed so that at about 30° C. or below, the genes needed for survival cease to be expressed and genes that actively cause cell death and lysis are expressed at high level. This can be accomplished by using promoters and regulatory elements that are regulated by temperature, or by adapting other regulatory systems to function in a temperature-dependent manner.

Temperature-regulated gene expression suitable for use in the Environmentally Limited Viability System are described by (Neidhardt et al., Annu. Rev. Genet. 18:295-329 (1984)). There are well-defined heat shock genes (Neidhardt et al. (1984)) that are well expressed at high temperature. Although the expression of these genes is temperature-regulated, there is frequently some low basal level of expression at the restrictive temperatures (Jones et al., J. Bacteriol. 169:2092-2095 (1987)). Temperature-regulated promoters exhibiting tighter control are described by (To be et al., Mol. Micro. 5:887-893 (1991), Hromockyi et al., Mol. Micro. 6:2113-2124 (1991), Qoronfleh et al., J. Bacteriol. 174:7902-7909 (1992)).

For essential genes, the S. flexneri virB promoter can be used, with S. flexneri virF gene and promoter elsewhere on the same plasmid, on a separate plasmid, or on the chromosome (Hromockyi et al. (1992); Tobe et al. (1991). A Yersina two component system for temperature regulation can also be used involving the structural gene for the temperature-regulated positive activator virF (Lambert de Rouvroit et al., Molec. Microbiol. 6:395-409 (1992) in combination with promoters of the yopH or yadR genes, with or without modification of the histone-like YmoA protein encoded by ymoA (Cornelis, in Molecular Biology of Bacterial Infections (Cambridge University Press, Cambridge, 1992)). The virF gene is equivalent to lcrF in Y. pestis (Hoe et al., J. Bacteriol. 174:4275-4286 (1992). Other promoters useful for expression of the essential gene can be identified by screening for cold-sensitive lack of expression of β-galactosidase in an S. typhimurium lacZ fusion library (Tanabe et al., J. Bacteriol. 174:3867-3873 (1992)). Many other repressor-promoter combinations can be adapted to express essential genes in a temperature-specific manner by using temperature-sensitive forms of the repressor. Methods for obtaining temperature-sensitive mutant repressors are well established.

The containment ability of the temperature regulated system can be further augmented by using promoters that function optimally at low temperatures and have minimal activity at 37° C., so that these promoters can be engineered to regulate the expression of the lethal genes or a repressor of the essential genes at low temperatures. Utilization of these promoters provides alternate controls of lethal genes and an additional means to eliminate any residual activity due to low level expression of an essential or replication gene at low temperatures.

Cold-specific expression can also be accomplished by coupling a gene to a cold-shock promoter or a cold-sensitive promoter. Cold shock promoters may be obtained from known cold-shock genes. Cold shock genes with promoters have been described (Jones et al. (1987)). Promoters with temperature-specific expression can be identified by a promoter probe vector. Such vectors have flanking DNA from a gene that is dispensable and which can readily be selected for or identified using, for example, a chromogenic substrate.

A preferred system that is less complex involves the interaction of the bacteriophage lambda promoters, $\lambda P_L$ and $\lambda P_R$, with the cI857 temperature-sensitive repressor. This system has been described, for example, by Lieb, J. Mol. Biol. 16:149-163 (1966). The lambda phage promoters $\lambda_L$ and $\lambda_R$, with their mutant temperature-sensitive repressor cI857, provide a tightly regulated system used in expression vectors to provide controlled expression of toxic genes (O'Connor and Timmis, J. Bacteriol. 169:4457-4462 (1987)). The cI857 gene product is synthesized but inactive at 37° C. and is synthesized but actively represses expression of genes at 30° C. and below whose transcription is controlled by either $\lambda P_L$ or $\lambda P_R$.

Leaky expression from the control sequences of an Environmentally Limited Viability System, if encountered, can be eliminated in several ways. The level of cI repressor produced can be increased by placing the cI857 gene under the control of a strong constitutive promoter, such as Ptrc, thus providing an excess of the thermosensitive repressor. In addition, more binding sites for the cI repressor can be introduced within the operator region of $\lambda P_R$ to reduce transcriptional starts at nonpermissive temperatures, or engineered into regions downstream of the promoter element to hinder transcription at lower temperatures. Additionally, an antisense RNA for the regulated gene could be transcribed from a differently regulated promoter oriented in the opposite direction to $\lambda P_R$.

E. Vectors

The disclosed Environmentally Limited Viability System will employ, unless otherwise indicated, conventional techniques of cell culture, molecular biology, microbiology, and recombinant DNA, which are within the skill of the art. Such techniques are explained fully in the literature. See, for example, Sambrook et al., *Molecular Cloning: A Laboratory Manual* (1989); *DNA Cloning*, Volumes I and II (Glover, ed., 1985); *Oligonucleotide Synthesis* (Gait ed., 1984); *Nucleic Acid Hybridization* (Hames and Higgins, eds., 1984); Perbal, *A Practical Guide To Molecular Cloning* (1984); the series, *Methods in Enzymology* (Academic Press, Inc.); Vectors: *A Survey Of Molecular Cloning Vectors And Their Uses* (Rodrigues and Denhardt, eds., Butterworths, 1987); Miller, *Experiments In Molecular Genetics* (Cold Spring Harbor Laboratory, 1972); and Miller, *A Short Course In Bacterial Genetics* (Cold Spring Harbor Laboratory, 1992).

As used herein, "vector" refers to an autonomously replicating nucleic acid unit. Many types of vectors are known with the most common and useful types being plasmid vectors, viral vectors, cosmid vectors, and phasmid vectors.

A diversity of vectors possessing different promoters, multiple cloning sequences, and different plasmid replicons can be used, so that the amount of a synthesized foreign antigen can be controlled by the relative number of gene copies. For example, vectors with p15A, pBR and pUC replicons can be constructed, all of which are dependent on the polA gene encoding DNA polymerase I for their replication. Preferably, vectors used in the Environmentally Limited Viability System do not use antibiotic resistance to select for maintenance of the vector.

Figure 3:
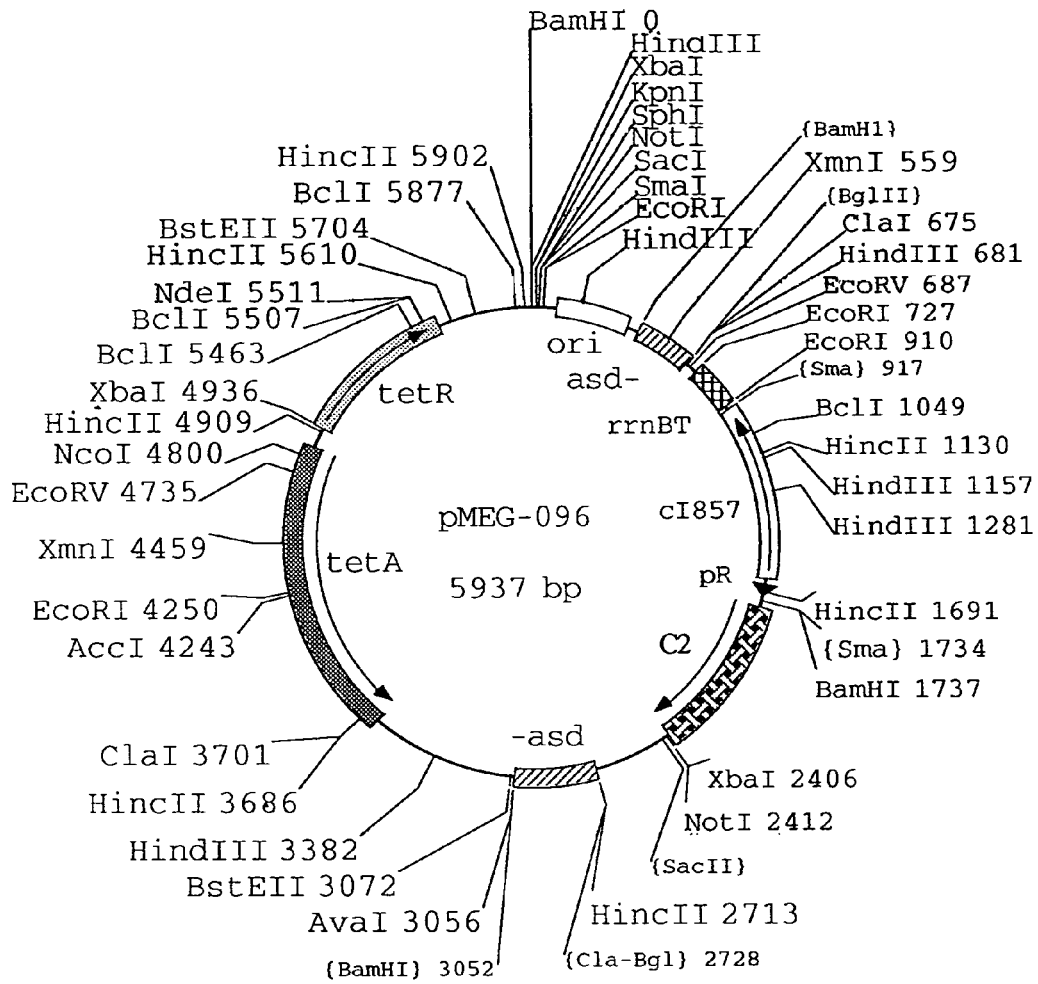
FIG. 3 is a diagram of the pir-dependent suicide vector pMEG-096 containing the bacteriophage P22 c2 repressor gene (C2) operatively linked to the bacteriophage lambda promoter right ($P_R$) and the bacteriophage lambda temperature sensitive repressor cI857 gene, both genes in a cartridge flanked by portions of the *S. typhimurium* asd gene (hatched with diagonal lines). This arrangement allows allele replacement of the wild-type chromosomal asd gene of any strain with homology to the flanking asd gene segments.

A preferred vector, pMEG-104, including both an essential gene and lethal gene is shown in FIG. 4. This vector is suitable for the expression of various foreign antigens in a recombinant avirulent *Salmonella*, and in other enteric bacteria modified by introduction of a defined asd deletion containing the repressor elements by using the suicide vector pMEG-096 (FIG. 3). Genes for such antigens can be cloned into the multiple cloning site and expressed under the control of the constitutive Ptrc. The host strain has the $\lambda$cI857 gene chromosomally located and constitutively expressed under the control of the native promoter ($P_{RM}$). The $\lambda$cI857 gene product is inactive at 37° C. and will not repress the $\lambda P_L$ which is driving the expression of the chromosomal P22 c2 wild-type gene (the c2 gene in P22 is equivalent to the d gene in lambda). The expression of the P22 c2 gene at 37° C. will repress the P22$P_R$ and thus preclude expression of the plasmid-encoded lysis genes 13 and 19. The asd gene in the plasmid vector will be expressed, however, since the $\lambda$cI857 protein is inactive at 37° C. and the asd gene will be expressed under the control of $\lambda P_L$. At 30° C. or lower, the $\lambda$cI857 protein exhibits a wild-type phenotype. It will repress the expression of the P22 c2 gene, which will therefore result in an insufficient quantity of c2 repressor and the lysis genes lys13 and lys19 will be expressed because of transcription initiated at the P22$P_R$. On the other hand, the functional $\lambda$cI857 gene product will now repress $\lambda P_L$ leading to cessation of synthesis of the asd gene product. It should be noted that the asd genes and the lysis genes lys13 and lys19 are arranged with no transcription terminations between them such that at 30° C. and below, the mRNA for the lysis genes lys13 and lys19 will extend into the asd gene but with an incorrect orientation and thus constitute an antisense RNA that will further eliminate expression of the asd gene. Just the opposite occurs at 37° C. such that the asd gene message will extend into the lysis genes 13 and 19 and serve as an antisense RNA to completely shut down the expression of the lysis genes. It should be noted that if the plasmid is transferred to another microorganism, the lysis genes will be expressed constitutively and lead to the demise of the recipient cell. Thus the containment host-vector system prevents both survival and spread of the microbial strain within the environment and transmission of recombinant plasmids within natural populations of bacteria.

Preferred bacterial hosts/strains and vectors useful in, or useful for constructing, Environmentally Limited Viability Systems are listed in Tables 1, 2, and 3.

TABLE 1

Strains and Plasmids Useful in the Construction and Confirmation of Environmentally Limited Viability Systems

| Strain | Description | Genotype |
|---|---|---|
| χ1891 | *E. coli* K-12 temperature sensitive polA mutant | F-thr txs purE supE42 λ- ΔtrpE his gyrA srl thyA57 T3$^r$ mtiA polA12$_{(ts)}$ cycA cycB |
| χ3730 | *S. typhimurium* LT-2 Asd$^-$ intermediate host strain that is reversibly rough and has three of the *S. typhimurium* host restriction systems inactivated. | leu hsdLT galE trpD2 tpsL120 ΔasdA1 Δ[zhf-4:Tn10] metE551 metA22 hsd5A hsdSB ilv |
| χ3761 | *S. typhimurium* UK-1 virulent wild-type strain obtained as a chicken passaged spleen isolate. | wild-type |
| MGN-026 | *E. coli* K-12 DH5α lysogenized with λpir from χ6151. This strain provides lacZα complementation and the ability to support pir-dependent replicons. This strain also transforms well, is an endonuclease mutant, and is recombination deficient, making it useful for recombinant work with the pGP704 derived suicide vectors. | endAl hsdR17 (rk–,mk+) supE44 thi-1 recAl gyrA relA1 Δ(lacZYA-argF) U169 λpir deoR (φ80dlacΔ(lacZ)M15) |
| MGN-336 | *E. coli* strain for the P22 lysis vectors obtained by electroporating χ6097 with pMEG-096 to provide a single integration of the c2 repressor genes in the asd gene. This provides the λP$_R$ driven P22 c2 gene and lambda cI857 between either part of the *S. typhimurium* asd deletion inserted into the chromosome, duplicating part of the asd gene of *E. coli* with that of *S. typhimurium*. | ara .(lac-pro) rpsL ΔasdA4 Δ[zhf-2::Tn10] Δasd-17::cI857PRc2 thi φ80dlacZΔM15 |
| MGN-377 | *S. typhimurium* UK-1 intermediate ELVS host strain obtained by electroporating χ3761 with large amounts of pMEG-096 (FIG. 3) to obtain a single integration of this cI857PR c2 clone in the asd gene. This provides the λP$_R$ driven P22 c2 gene and λcI857 between either part of the *S. typhimurium* asd deletion duplicating portions of the wild-type asd gene in the chromosome. | wild-type + integrated pMEG-096 |

TABLE 1-continued

Strains and Plasmids Useful in the Construction and Confirmation of Environmentally Limited Viability Systems

| Strain | Description | Genotype |
|---|---|---|
| MGN-391 | S. typhimurium UK-1 ELVS host obtained from MGN-377 by selecting for fusaric acid resistant, tetracycline sensitive, Asd⁻ isolates produced by excision of pMEG096 in MGN-377 leaving the cI857PRc2 cartridge in the defined asd deletion. Sibling of MGN-392 (Table 3). | Δasd-17::cI857PRc2 |
| MGN-399 (pMEG-100 + pYA232) | S. typhimurium UK-1 ELVS host MGN-392 containing the intermediate ELVS vector pMEG-100 (FIG. 5), and the lac$^q$ repressor plasmid pYA232 (Table 2). Obtained by electroporating MGN-392 with pMEG-100 and pYA232. Does not grow at temperatures below 30° C. | (pMEG-100 + pYA232) Δasd-17::cI857PRc2 |
| MGN-401 (pYA292) | S. typhimurium UK-1 ELVS host MGN-392 electroporated with the Asd⁺ vector pYA292 to provide a positive control for growth of this strain at different temperatures without DAP. | (pYA292) Δasd-17::cI857PRc2 |
| MGN-409 | E. coli K-12 strain MGN-336 electroporated with ELVS vector pMEG-104 (FIG. 4) This construct does not grow at temperatures below 30° C. | ara Δ(lac-pro) rpsL, ΔasdA4 Δ[zhf-2::Tn10] Δasd-17::cI857PRc2 thi φ80dlacZDMI5 |

TABLE 2

Plasmids Useful in the Construction and Confirmation of Environmentally Limited Viability Systems

| Plasmid | Description | Genotype |
|---|---|---|
| pMEG-011 | A pir-dependent suicide vector with lacZα multiple cloning site derived from pGP704. | |
| pMEG-072 | The promoter right of P22HTint, PCR amplified and cloned as a 125 by BamHI-SalI fragment into the BamHI-SalI sites of pKK232-8 | |
| pMEG-076 | The promoter left of lambda PCR amplified from the lambda lysogen x2869 and cloned as a 163 by fragment into the SmaI-BamHI sites of pKK232-8 | |
| pMEG-078 | The P22HTint lysis genes lys13 and lys19 PCR amplified as a 797 by fragment with a SD site at a 5' blunt end and a PstI site designed into the 3' end, cloned into the EcoRV-PstI sites of the low copy vector pWKS30 | |
| pMEG-086 | An Asd⁺ clone obtained by inserting the 314 to 1421 bp asd PCR product lacking the promoter and SD regions as a 1115 by BglII - blunt fragment, into the BamHI-PvuII sites of pMEG-076. This places asd under the regulation of $\lambda P_L$ | |
| pMEG-088 | A PCR clone of the P22 c2 gene driven by XPR and controlled by λcI857. | |
| pMEG-089 | The 1060 by SalI-PvuII fragment of pMEG-078 containing the P22 lysis genes lys13 and lys19 driven by the P22 promoter right cloned into the SalI-PvuII sites of pMEG-072. This construct is toxic unless in a strain expressing P22 c2 repressor | |
| pMEG-090 | Intermediate expression vector obtained by BglII partial digestion of pYA810, isolating the 1.6 kb fragment containing the p15A origin of replication, Ptrc, multiple cloning site and 5ST1T2, and ligating to the 1.3 kb BamHI Km$^r$ cartridge of pUC-4K | |
| pMEG-096 | The ~2.05 kb ClaI fragment of pMEG-088 ligated into the BglII site of pMEG-006 following treatment with T4 DNA polymerase. This provides the $\lambda P_R$ driven P22 c2 gene and cI857 between either part of the S. typhimurium asd deletion allowing for chromosomal insertion. | |
| pMEG-097 | The 1277 by EcoRI-XbaI fragnment of pMEG-86 containing the $\lambda P_L$asd gene cloned into the PvuII-XbaI sites of pMEG-89 using the trpA terminator linker with an internal BglII site and an EcoRI end. This construct is lethal if not in a host with a P22 c2 repressor. | |
| pMEG-098 | Derived from pMEG-097 by removing the 28 by PstI-XbaI fragment of pMEG-097 treating with T4 DNA polymerase, and religating. | |
| pMEG-100 | ELVS expression vector intermediate obtained by ligating the 2.26 kb BamHI-BglII fragment of pMEG-098 containing the asdlysis cartridge into the BglII site of pMEG-090. | |
| pMEG-104 | ELVS p15A expression vector obtained by deleting the 1.36 kb SalI fragment of pMEG-100 containing the Km$^r$ cartridge. Requires host with P22 c2 repressor. | |
| pYA232 | Tc$^r$, lacI$^q$repressor on pSC101 vector | |
| pYA248 | p15A Asd⁺ expression vector, using S. mutans asd gene (Nakayama et al. 1988). | |
| pYA292 | p15A Asd⁺ expression vector, using S. typhimurium asd gene (Galan et al. 1990). | |

TABLE 2-continued

Plasmids Useful in the Construction and Confirmation of Environmentally Limited Viability Systems

| Plasmid | Description | Genotype |
|---|---|---|
| pYA810 | p15A Asd+ expression vector, using *S. typhimurium* asd gene. Derived from pYA292 by removing the HindIII fragment of the multiple cloning site containing the lacZα gene. | |

F. Microbial Hosts

Any bacteria in which an essential gene is known for which mutants can be made, or for which a lethal gene is available, can serve as the host for an Environmentally Limited Viability System. Generally, those bacteria that are normally found in a target environment would be used in an Environmentally Limited Viability System targeted to that environment. It is preferred that promoters and regulatory elements of the system be native for the host being used, but this is not required. For example, many bacterial promoters are functional in heterologous hosts. Preferred host cells useful in, or useful for constructing, Environmentally Limited Viability Systems are listed in Tables 1 and 3.

1. Obtaining defective mutants. Defective mutants can be obtained as described above. For example, deletion mutations in the asd gene (Δasd) can be made in a diversity of bacterial strains that are members of the Enterobacteriaceae, and in other gram-negative bacteria and mycobacteria. *E. coli* K-12 and *S. typhimurium* LT-2 strains can be used to isolate asd mutants and their derivatives; the Asd⁻ strains can be used to construct other strains, utilizing transposon techniques, as described infra. Asd⁻ strains are also described in U.S. Pat. No. 4,190,495.

Standard mutagenesis and mutant enrichment protocols are not efficient for the recovery of asd mutants, since a mutant with a requirement for DAP undergoes lysis and death in the absence of DAP. In a synthetic medium, asd mutants require L-methionine, L-threonine, and DAP for growth. The requirement for L-methionine and L-threonine is satisfied by homoserine, which is a common precursor to both methionine and threonine. Mutagenesis of an *E. coli* or *S. typhimurium* strain followed by an ampicillin-cycloserine procedure for the enrichment of auxotrophic mutants seldom, if ever, recovers mutants with a sole requirement for homoserine. Curtiss et al. (1965) describe a cycloserine-enrichment procedure for selecting auxotrophs. The reason that homoserine-requiring auxotrophs are seldom isolated is that β-aspartic semialdehyde is converted to homoserine by either of two dehydrogenases which are encoded in two genes. The probability of inactivating both genes in a single cell is exceedingly small, and thus the homoserine-requiring auxotrophs may not be detected by random screening techniques.

This problem is overcome by the inclusion of DAP in all media during mutagenesis, and by enrichment or selection using the ampicillin-cycloserine technique. This leads to the recovery of asd mutants that require both homoserine and DAP. Ampicillin and cycloserine both inhibit cell wall synthesis in growing cells capable of protein synthesis, but are without effect on auxotrophic mutants unable to synthesize proteins because of the absence of nutritional requirements. asd mutant strains Chi3008 and Chi2108, which are *S. typhimurium* and *E. coli* strains, respectively, were isolated using this procedure. The Asd⁻ phenotype of Chi3008 is due to a point mutation in the asd gene, and thus the frequency reversion to Asd⁺ is fairly high. On the other hand, the Asd⁻ phenotype of Chi2108 results from a deletion in the asd gene, thus, the reversion frequency is very low.

Figure 2:
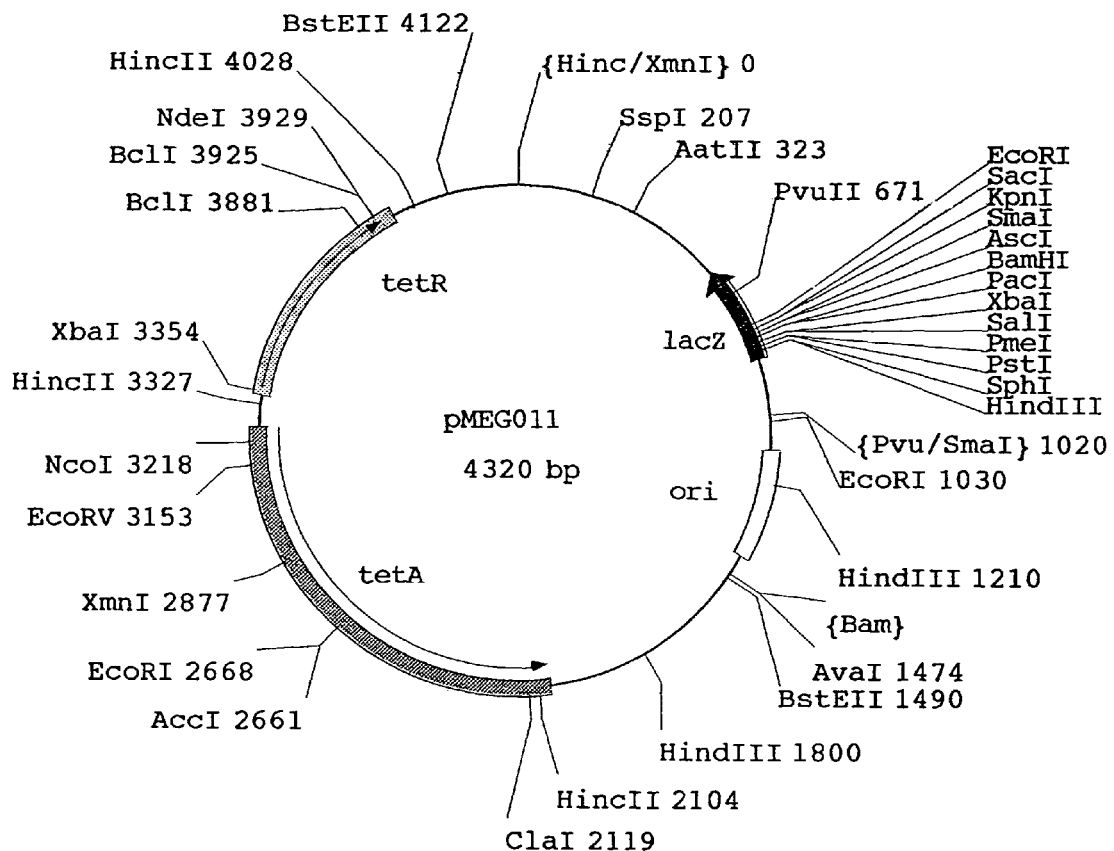
FIG. 2 is a diagram of pir-dependent suicide vector pMEG-011 which is unable to replicate in any host lacking a functional pir gene. The vector contains the multiple cloning site from the commercially available cloning vector pNEB193, providing a number of unique cloning sites and the blue/white screen associated with the lacZ a gene in an appropriate host. The vector also contains the tetracycline resistance gene (tetA) from transposon Tn10, allowing selection for tetracycline resistance with integration into the chromosome and then selection against the integrated vector on media containing fusaric acid, facilitating replacement of wild-type genes with modified genes containing deletions and insertions.

Deletion mutations containing insertions of foreign genes encoding regulatory elements for an ELVS can be introduced into the bacterial chromosome using well known recombinant DNA techniques. For example, the gene to be deleted should first be cloned onto a suicide vector such as pMEG-011 (FIG. 2). pMEG-011 is a pir-dependent suicide vector derived from pGP704 (Miller et al., *J. Bacteriol.* 170:2575-2583 (1988)). The replication of such a suicide vector is dependent on the production of a functional pir gene product by the host strain. When the suicide vector is transferred to a strain lacking the pir gene, the only means of maintaining the suicide vector is by recombination integrating the suicide vector into the host chromosome. The presence of the gene to be deleted on the suicide vector results in homologous recombination of the suicide vector into the corresponding gene on the chromosome. This integration will result in a deletion in the gene of interest if the wild type gene on the suicide vector has been altered by deletion of internal regions of the gene prior to integration. This can be accomplished by either restriction enzyme digestion or inverse PCR amplification. The vector-borne gene of interest is thus inactivated while leaving sufficient flanking DNA to allow recombination into the chromosome. The defined deletion produced in the suicide vector can be designed to provide a convenient restriction enzyme cloning site allowing the insertion of any foreign gene, including the regulatory genes needed for the Environmentally Limited Viability System. After the initial single recombination event integrating the suicide vector into the chromosome, a second recombinational event can be selected for by selection against the tetracycline element of the suicide vector on media containing fusaric acid (Bochner et al., *J. Bacteriol.* 143:926 (1980)). This results in the replacement of the wild-type allele with the deleted gene containing the desired insert. These methods have been used to produce defined deletions and insertion of foreign genes into the chromosome of *Salmonella* strains (Chatfield et al., *Vaccine* 10:53-60 (1992)).

Although the preferred embodiment of the disclosed ELVS is a live bacterial vaccine, the ELVS can be used with any microbe in which ELVS components, as described above, can be obtained and adapted to that microbe. In particular, an ELVS will be useful when used in conjunction with the production of valuable products in fermenters, especially products that might be toxic or otherwise harmful if the bacteria producing them escaped and survived.

2. Live bacterial vaccines. Preferred hosts for use as vaccines are enteric bacteria. As used herein, enteric bacteria refers to any Enterobacteraceae. Many of the preferred genes and regulatory elements described above are operable in most enteric bacteria, thus allowing use of the many well developed *E. coli* and *Salmonella* regulatory systems. Most preferably, the bacterial host is an avirulent *Salmonella*.

In one embodiment of the system described herein, an avirulent derivative of a pathogenic microbe that attaches to, invades and persists in the gut-associated lymphoid tissue (GALT) or bronchial-associated lymphoid tissue (BALT) is used as a carrier of the gene product which is used for stimulating immune responses against a pathogen or allergen. Avirulent does not mean that a microbe of that genus or species can not ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Avirulent *Salmonella* containing an ELVS can be used to protect animals and humans against *Salmonella* infection. To be useful, such strains need not express any foreign antigen. Recombinant avirulent *Salmonella* vaccines expressing protective antigens from bacterial, viral, mycotic and parasitic pathogens that are efficacious in inducing immunities to protect against infections by these pathogens will be more acceptable and receive more widespread use if rendered safer by biological containment properties that preclude survival and proliferation in the environment. The developments proposed should potentiate the commercial value of vaccine technology based on the use of live bacterial vaccine vectors.

3. Avirulent Bacterial Hosts. To be useful as a live recombinant vaccine, the bacterial host must be avirulent. Strains of different *Salmonella* serotypes can be rendered avirulent and immunogenic by methods known to those skilled in the art, for example, 1) by introducing mutations that impose a requirement for aromatic amino acids and vitamins derived from precursors in this pathway (Stocker et al. (1983), Hoiseth and Stocker (1981)), 2) by deleting genes for global regulators such as cya and crp (Curtiss and Kelly (1987)), phoP (Miller et al., *Proc. Natl. Acad. Sci. USA* 86:5054-8 (1989), Galan and Curtiss, *Microb. Pathogen.* 6:433-443 (1989)), and ompR (Dorman et al., *Infect. Immun.* 57:2136-40 (1989)), 3) by deleting genes for lipopolysaccharide (LPS) synthesis, such as by galE (Germanier and Furer, *Infect. Immun.* 4:663-73 (1971), Germanier and Furer, *J. Infect. Dis.* 131:553-8 (1975)), although this alone may be insufficient (Hone et al., *Infect. Immun.* 56:1326-1333 (1988)), 4) by mutating genes needed for colonization of deep tissues, such as cdt (Kelly et al., *Infect. Immun.* 60:4881-4890 (1992); Curtiss et al., *Devel. Biol. Stand.* 82:23-33 (1994)), or 5) by preventing expression of genes for proteases required at high temperature, such as htrA (Johnson et al., *Mol. Microbiol.* 5:401-407 (1991). Strains possessing mutations in phoQ (Miller et al., *Proc. Natl. Acad. Sci. USA* 86:5054 (1989)) have the same phenotype as mutations in phoP. Hereinafter strains with mutations in either phoP or phoQ are referred to collectively as phoP mutants. It is preferred that mutations in the above described genes be introduced as deletions since this will preclude reversion mutations and enhance the safety of vaccine strains containing them. Subsequent to the discovery that *Salmonella* strains with mutations in the genes described above are avirulent and immunogenic, it was observed that many of these strains exhibited, after oral administration, nearly wild-type abilities to invade and persist in the GALT and to colonize other lymphoid tissues such as mesenteric lymph nodes, liver, and spleen, but without causing disease symptoms. As a consequence, these attenuated vaccine strains are capable of stimulating strong mucosal, systemic and cellular immune responses in immunized animal hosts that confer protective immunity to challenge with virulent wild-type *Salmonella* strains. Any of these avirulent *Salmonella* can be endowed with the ability to express important colonization or virulence antigens from other bacterial, viral, mycotic and parasitic pathogens at a high level within an immunized animal host (Clements, *Pathol. Immunopathol. Res.* 6:137-146 (1987); Dougan et al., *Parasite Immun.* 9:151-60 (1987); Chatfield et al., *FEMS Immunol. Med. Microbiol.* 7:1-7 (1993); Curtiss et al., in *Virulence mechanisms of bacterial pathogens*, (Roth, American Society for Microbiology, Washington, D.C., 1988) pages 311-328; Curtiss et al., *Dev. Biol. Stand.* 82:23-33 (1994); Doggett and Curtiss, *Adv. Exp. Med. Biol.* 327:165-73 (1992); Schodel, *Semin Immunol.* 2:341-9 (1990)).

G. Expression Genes

One of the primary uses of the disclosed Environmentally Limited Viability System is to allow recombinant expression of a desired expression product limited to a specific permissive environment. As used herein, expression gene refers to a gene expressed in an ELVS that encodes a desired expression product. Expression of a gene means that the information inherent in the structure of the gene (the sequence of DNA bases) is transformed into a physical product in the form of an RNA molecule, polypeptide or other biological molecule by the biochemical mechanisms of the cell in which the gene is located. The biological molecule so produced is called the expression product. The term expression product as used here refers to any biological product or products produced as a result of the biochemical reactions that occur under the control of a gene. The expression product may be, for example, an RNA molecule, a peptide, or a product produced under the control of an enzyme or other molecule that is the initial product of the gene, that is, a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all expression products as the term is used here. Such expression products need not be heterologous to the host cell nor encoded by a recombinant gene. It is preferred, however, that the expression gene is recombinant. Most preferably, the expression gene encodes an antigen.

Expression of the expression gene can be accomplished, for example, by inserting the coding sequence encoding a desired gene product in the multiple cloning site of the ELVS vector pMEG-104 (FIG. 4). This places the coding sequence of the expression gene under control of the constitutive promoter Ptrc, with transcription terminating at rrnB thus preventing inappropriate transcription of the lysis genes.

Vaccine Antigens.

Live recombinant vaccines using an Environmentally Limited Viability System can be used to deliver any antigen that can be expressed in the host microorganism. For example, antigens can be from bacterial, viral, mycotic and parasitic pathogens, to protect against bacterial, viral, mycotic, and parasitic infections, respectively; gametes, provided they are gamete specific, to block fertilization; and tumor antigens, to halt cancers. The selection and recombinant expression of antigens has been previously described by Schodel (1992) and Curtiss (1990). Immunogenicity of the vaccines can be augmented and/or modulated by constructing strains that also express genes for cytokines.

Some examples are vaccines for the control of plague caused by *Yersinia pestis*, of gonorrhea caused by *Neisseria* gonorrhoea, of syphilis caused by *Treponema pallidum*, and of venereal diseases as well as eye infections caused by *Chlamydia trachomatis*. Species of *Streptococcus* from both group A and group B, such as those species that cause sore throat or heart diseases, *Neisseria meningitidis, Mycoplasma pneumoniae, Hemophilus influenza, Bordetella pertussis, Mycobacterium tuberculosis, Mycobacterium leprae, Bordetella avium, Escherichia coli, Streptococcus equi, Streptococcus pneumonias, Brucella abortus, Pasteurella hemolytica, Vibrio cholera, Shigella* species, and *Legionella pneumophila* are additional examples of bacteria within the scope of this invention from which genes could be obtained. Viral antigens can also be used with the Environmentally Limited Viability System. Viral antigens can be used in vaccines directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, or Retrovirus. Vaccines using antigens of pathogenic fungi, protozoa and parasites can also be used.

The antigen can also be an allergen of the host such as antigens from pollen and animal dander. Such an antigen can be used in the Environmentally Limited Viability System in an exposure regimen designed to specifically desensitize an allergic host.

Recombinant avirulent *Salmonella* vaccines are capable of stimulating strong mucosal, systemic and cellular immune responses against the foreign antigens and thus against the pathogen that is the source of the foreign antigen. It is not necessary that the antigen gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus a gene as defined and claimed here is any unit of heredity capable of producing an antigen. The gene may be of chromosomal, plasmid, or viral origin.

Multiple antigens can also be expressed by a recombinant avirulent *Salmonella* vaccine. In addition, antigens, or even parts of antigens, that constitute a B cell epitope or define a region of an antigen to which an immune response is desired, can be expressed as a fusion to a carrier protein that contains a strong promiscuous T cell epitope and/or serves as an adjuvent and/or facilitates presentation of the antigen to enhance, in all cases, the immune response to the antigen or its component part. This can easily be accomplished by genetically engineering DNA sequences to specify such fusions for expression by avirulent vaccine strains. Fusion to tetanus toxin fragment C, CT-B, LT-B and hepatitis virus B core are particularly useful for these purposes, although other epitope presentation systems are well known in the art.

In order for the expression gene to be effective in eliciting an immune response, the expression gene must be expressed, which can be accomplished as described above. In order for a vaccine to be effective in immunizing an individual, the antigenic material must be released in such a way that the immune system of the vaccinated animal can come into play. Therefore the live avirulent microorganism must be introduced into the animal. In order to stimulate a preferred response of the GALT or BALT cells as discussed previously, introduction of the microbe or gene product directly into the gut or bronchus is preferred, such as by oral administration, gastric intubation or in the form of aerosols, although other methods of administering the vaccine, such as intravenous, intramuscular, subcutaneous injection or intramammary or intrapenial or vaginal administration, is possible.

H. Vaccine Compositions

Oral immunization in a suitable animal host with live recombinant immunization *Salmonella* vaccine strains leads to colonization of the gut-associated lymphoid tissue (GALT) or Peyer's patches, which leads to the induction of a generalized mucosal immune response to both *Salmonella* antigens and the foreign antigens synthesized by the recombinant *Salmonella* (Curtiss et al., *Adv. Exp. Med. Biol.* 251:33-47 (1989)). Further penetration of the vaccine strain into the mesenteric lymph nodes, liver and spleen augments the induction of systemic and cellular immune responses directed against *Salmonella* antigens and the foreign antigens made by the recombinant *Salmonella* (Doggett and Curtiss (1992)). Thus the use of recombinant avirulent *Salmonella* vaccines for oral immunization stimulates all three branches of the immune system, particularly important when immunizing against infectious disease agents which colonize on and/or invade through mucosal surfaces.

By vaccine is meant an agent used to stimulate the immune system of a living organism so that an immune response occurs. Preferably, the vaccine is sufficient to stimulate the immune system of a living organism so that protection against future harm is provided. Immunization refers to the process of inducing a continuing high level of antibody and/or cellular immune response in which T-lymphocytes can either kill the pathogen and/or activate other cells (for example, phagocytes) to do so in an organism, which is directed against a pathogen or antigen to which the organism has been previously exposed. Although the phrase "immune system" can encompass responses of unicellular organisms to the presence of foreign bodies, that is, interferon production, as used herein the phrase is restricted to the anatomical features and mechanisms by which a multi-cellular organism responds to an antigenic material which invades the cells of the organism or the extra-cellular fluid of the organism. The antibody so produced may belong to any of the immunological classes, such as immunoglobulins A, D, E, or M. Of particular interest are vaccines which stimulate production of immunoglobulin A (IgA) since this is the principle immunoglobulin produced by the secretory system of warm-blooded animals, although the vaccines described herein are not limited to those which stimulate IgA production. For example, vaccines of the nature described herein are likely to produce a broad range of other immune responses in addition to IgA formation, for example, cellular and humoral immunity. Immune responses to antigens are well studied and widely reported. A survey of immunology is given in Barrett, *Textbook of Immunology*, Fourth Edition, (C. V. Mosby Co., St. Louis, Mo., 1983), Sites et al., *Basic and Clinical Immunology* (Lange Medical Books, Los Altos, Calif., 1994), and Orga et al., Handbook of Mucosal Immunology (Academic Press, San Diego, Calif., 1994). Mucosal immunity is also described by McGhee and Mestecky, *The Secretory Immune System*, Ann. N.Y. Acad. Sci., Volume 409 (1983).

An individual treated with a vaccine of the invention is defined herein as including all vertebrates, for example, mammals, including domestic animals and humans, various species of birds, including domestic birds, particularly those of agricultural importance. Preferably, the individual is a warm-blooded animal.

The dosages of live recombinant vaccines required to elicit an immune response will vary with the antigenicity of the cloned recombinant expression product and need only be a dosage sufficient to induce an immune response typical of existing vaccines. Routine experimentation will easily establish the required dosage. Typical initial dosages of vaccine for oral administration could be $1 \times 10^7$ to $1 \times 10^{11}$ CFU depending upon the size and age of the individual to be immunized. Administering multiple dosages can also be used as, needed to provide the desired level of protective immunity. The pharmaceutical carrier in which the vaccine is suspended can be any solvent or solid material for encapsulation that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc or sucrose, or animal feed. Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

I. Adaptation of Environmentally Limited Viability Systems to Useful Host Strains.

Avirulent strains of *S. typhimurium* are known to be totally attenuated and highly immunogenic in mice, chickens, and pigs, inducing protective immunity to infection with 10,000 times a lethal dose with the virulent wild-type strain. Similarly, avirulent strains of *S. choleraesuis* are attenuated and immunogenic in mice and pigs and also offer significant protective immunity. Avirulent strains of *S. dublin* have been isolated and tested and found to be avirulent, immunogenic, and protective in calves. Attenuated *S. typhi* strains have also been constructed and found to induce significant immune responses in human volunteers. Attenuated derivatives of *Vibrio cholerae* and *Shigella flexneri* have also been constructed and used as vaccines to induce significant immune responses in human volunteers. *Mycobacterium bovis* strain BCG has also been used to orally immunize humans. Attenuated *Listeria monocytogenes* has also been used as a live vaccine for immunization of mice. In addition to serving as vaccines to immunize animals and human hosts against infection with related virulent wild-type strains, avirulent derivatives of the above cited microorganisms can also be used as antigen delivery vectors by genetically engineering them to express foreign antigens. These antigens could be from bacterial, viral, fungal and parasitic pathogens or they could be allergens or they could be gamete specific antigens in a contraceptive vaccine or tumor antigens in anti cancer vaccines. Immunization of animal and/or human hosts with these live recombinant avirulent vaccines is known to induce mucosal, systemic and cellular immune responses directed against the foreign antigen and against the pathogen from which the gene specifying the foreign antigen was isolated or against allergens or against sperm or ova or against tumor cells, respectively.

Bacterial pathogens can be attenuated by introducing deletion ($\Delta$) mutations in various genes as described above or as known to those knowledgeable in the art. Any of these strains are suitable for introduction of an ELVS of the sort disclosed herein, although modifications would be needed to make the system operable in gram-positive bacteria. Specifically these modifications would require modification of Shine-Dalgarno sequences to permit translation of mRNA, slight changes in promoter sequences to cause transcription to be more efficient, and, in the case of all gram-positive genera other than *Mycobacteria*, the asd gene would need to be replaced by some other essential gene. This is because DAP is not contained in the rigid layer of the cell wall of most gram-positive bacterial genera except for the *Mycobacteria*. On the other hand, there are numerous essential genes for essential components of the cell wall, cell membranes, and for maintaining the integrity of DNA that could be used in both gram-positive and gram-negative bacteria. The components of the ELVS described in FIG. 4 can readily be introduced into *Salmonella* species, *E. coli*, *Shigella* species and other enterics. For example the suicide vector pMEG-096, can be transferred from a pir-containing donor strain to an attenuated vaccine candidate with a wild-type asd gene. Integration of the cI857PRc2 cartridge of pMEG-096 into the candidate strain can be accomplished by first selecting tetracycline resistant clones that have integrated pMEG-096, and then growing the cells on fursaric acid-containing media to select for cells that have lost the wild-type asd gene in favor of the asd defined deletion containing the cI857PRc2 cartridge. These manipulations are described in the examples below. A derivative of pMEG-104 (FIG. 4) containing a gene encoding a desired foreign antigen, could then be introduced by electroporation. The resulting recombinant avirulent vaccine with its ELVS can then be used to immunize suitable hosts. Excretion or shedding of any live vaccine cells by the vaccinated hosts will activate the ELVS which will lead to death by lysis of these vaccine cells. This will preclude the survival of the vaccine outside of the host animal and thus eliminate the possibility for immunization of individual hosts that did not elect to be immunized.

DEPOSITS OF STRAINS USEFUL IN PRACTICING THE INVENTION

A deposit of biologically pure cultures of the following strains (Table 3) were made with the American Type Culture Collection, 12301 Parklawn Drive, Rockville, Md. The accession number indicated was assigned after successful viability testing, and the requisite fees were paid. Access to the cultures will be available during pendency of the patent application to one determined by the Commissioner to be entitled thereto under 37 CFR 1.14 and 35 USC 122. All restriction on availability of the cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, which-ever is longer. Should a culture become nonviable or be inadvertently destroyed, or, in the case of plasmid-containing strains, loose its plasmid, it will be replaced with a viable culture(s) of the same taxonomic description.

strong trc promoter, multiple cloning site used in existing Asd+ vectors, and the ribosomal transcription terminators 5S T1 T2 to prevent transcriptional interference from the trc promoter. Many of these vector components were obtained by

TABLE 3

Strains Deposited with ATCC for Implementation of Enviromentally Limited Viability System

| Strain (plasmid) | ATCC No. | Deposit Date | Description | Genotype |
|---|---|---|---|---|
| MGN-318 (pMEG-096 | | Jun. 6, 1995 | E. coli MGN-026 containing pMEG-096. pMEG-096 (FIG. 3) contains the $\lambda P_R$ driven P22 c2 repressor gene and $\lambda$cI857 repressor gene on a 2.05 kb ClaI fragment from pMEG-088 treated with T4 DNA polymerase and ligated into the BglII site of the asd deletion vector pMEG-006 following treatment with T4 DNA polymerase and CIAP. This provides the $\lambda P_R$ driven P22 c2 gene and XcI857 repressor gene between either end of the S. typhimurium asd deletion allowing insertion into the chromosome. | (pMEG-096 asd-17::cI857PRc2) endA1 hsdR17 (rk−, mk+) supE44 thi-1 recA1 gyrA relA1 (lacZYA-argF) U169 $\lambda$pir deoR ($\phi$80dlac (lacZ)M15) |
| MGN-392 | | Jun. 6, 1995 | S. typhimurium UK-1 ELVS host obtained from MGN-377 by selecting for fusaric acid resistant, tetracycline sensitive, Asd isolates produced by excision of pMEG-096 in MGN-377 leaving the cI857PRc2 cartridge in the defined asd deletion. | asd-17::cI857PRc2 |
| MGN-417 (pMEG-104) | | Jun. 6, 1995 | S. typhimurium UK-1 ELVS host MGN-392 electroporated with the ELVS expression vector, pMEG-104 (FIG. 4), an asdlysis p15A expression vector obtained by deleting the 1.36 kb SalI fragment of pMEG-100 (Table 2, FIG. 5) containing the Km$^r$ cartridge. This construct does not grow at temperatures below 30° C. Plasmid requires host with functional P22 c2 gene. | (pMEG-104 P22$P_R$ lys13 lys19 asd $\lambda P_1$) asd-17::cI857PRc2 |

Described below are examples of the present invention which are provided only for, illustrative purposes, and not to limit the scope of the present invention. In light of the present disclosure, numerous embodiments within the scope of the claims will be apparent to those of ordinary skill in the art.

EXAMPLES

Example 1

Construction of a Plasmid Based Thermoregulated Environmentally Limited Viability System The methods used to produce the components of the ELVS illustrated in FIG. 4 employed standard molecular cloning techniques. The ELVS depicted in FIG. 4 consists of two main components. The first component is the ELVS vector which combines the application of a temperature regulated essential gene, asd, with the temperature regulated lethal genes, lys13 and lys19, oriented in a manner to provide additional regulation by antisense RNA for both essential and lethal genes. The second component is the ELVS host required to maintain the ELVS vector, which for the S. typhimurium examples used the host MGN-392, possessing a defined asd deletion with a thermosensitive cI857 and c2 repressor cartridge insert.

The ELVS expression vector pMEG-104, was constructed by the assembly of six individual components consisting of 1) the S. typhimurium asd gene, 2) the bacteriophage lambda promoter left to drive the asd gene, 3) the bacteriophage P22 lysis genes lys13 and lys19, 4) the bacteriophage P22 promoter right to drive the lysis genes, 5) the trpA terminator to prevent transcription from external promoters, and 6) the expression vector core obtained from pYA810 (Galan et al. (1990)), consisting of the p15A origin of replication, the PCR amplification as described below, followed by modification of the DNA ends with either restriction enzymes or polymerases to allow assembly of the intermediate constructs. The asd gene of S. typhimurium was obtained by PCR amplification of the region between nucleotides 314 to 1421 of the S. typhimurium asd sequence as found on pYA292 (Galan et al. (1990)). This asd PCR product, a 1115 by fragment with one end blunt and the other having a BglII overhang and lacking the promoter and Shine-Dalgarno regions of the asd gene, was cloned into the lambda promoter left vector, pMEG-076, in an orientation to produce an asd gene driven by the bacteriophage lambda promoter left. The result is plasmid pMEG-086.

The promoter left of bacteriophage lambda present on pMEG-076 was obtained by PCR amplification of the region between nucleotides 5 to 160 of the promoter left sequence (Giladi et al., J. Mol. Biol. 231:109-121 (1990)). The resulting 155 by fragment, with a blunt end and a BamHI end, was cloned into the SmaI to BamHI sites of the promoter probe cloning vector pKK232-8 (Brosius, J. Gene 27:151 (1984)), resulting in vector pMEG-086. In this vector, the asd gene is driven by the lambda promoter left.

The 1277 by EcoRI to XbaI fragment of pMEG-086 containing the $\lambda P_L$ driven asd gene was then sub-cloned into the PvuII to XbaI sites of the bacteriophage P22 PR lys13 lys19 vector pMEG-089 using a synthetic trpA terminator, containing an internal BglII site and an EcoRI end, to produce pMEG-097. The relative orientation of the transcriptional elements for asd and lys13 lys19 in pMEG-097 results in convergent transcription which produces antisense RNA for the asd and lys genes at differential temperatures.

The bacteriophage P22 lysis genes used in the construction of pMEG-097 were obtained by PCR amplification of nucleotides 62 to 850 of the P22 lysis gene region (Rennell et al.,

*Virology* 142:280-289 (1985)). The resulting 797 by fragment, with an introduced Shine-Dalgarno site, a 5' blunt end, and a PstI site designed into the 3' end, was cloned into the EcoRV to PstI sites of the low copy-number vector pWKS30 (Kushner, S. *Gene* 100:195-199 (1990)). The resulting vector, pMEG-078, has the lys13 and lys19 genes under control of the lac promoter. The lysis genes were then sub-cloned as a 1060 by SalI to PvuII fragment from pMEG-078 into the SalI to PvuII sites of the P22 promoter right expression vector, pMEG-072. In the resulting vector, pMEG-089, the bacteriophage P22 lysis genes lys13 lys19 are driven by the P22 promoter right. The bacteriophage P22 promoter right in pMEG-072 was obtained by PCR amplification of the region between nucleotides 23 and 138 of the P22 promoter right sequence (Poteete et al., *J. Mol. Biol.* 137:81-91 (1980)). The resulting 125 by BamHI to SalI fragment was cloned into the BamHI to SalI sites of the promoter probe vector pKK232-8 (Brosius, J., *Gene* 27:151 (1984)) to produce pMEG-072.

The asd lys13 lys19 cartridge present in pMEG-097 contains both the essential and lethal genes separated by a portion of the multiple cloning site, including a BamHI site from previous manipulations. This region was deleted from pMEG-097 as a 28 by PstI-XbaI fragment, and the remaining vector was treated with T4 DNA polymerase prior to religating. This resulted in vector pMEG-098, containing the asd lys13 lys19 cartridge. The asd lys13 lys19 cartridge was then transferred to the expression vector core of pMEG-090 by digesting pMEG-090 with BglII and inserting the 2.26 kb BamHI to BglII fragment of pMEG-098 containing the asd lys13 lys19 cartridge. This produced pMEG-100, shown in FIG. 5.

Vector pMEG-090 was derived from pYA810 by performing a partial BglII digest of pYA810; isolating the 1.6 kb fragment of pYA810 containing the p15A origin of replication, the trc promoter, and the multiple cloning site with the transcriptional terminator; and ligating the fragment to the 1.3 kb BamHI kanamycin resistance element of pUC-4K (Christie G. E., et al., *Proc. Natl. Acad. Sci. USA* 78:4180 (1981)).

In pMEG-100, the essential and lethal genes are flanked by two different transcriptional terminators, the first is the trpA terminator (Christie et al., *Proc. Natl. Acad. Sci. USA* 78:4180 (1981)) and the other is the ribosomal 5S terminator repeat cartridge used in the previously described Asd$^+$ balanced-lethal vectors pYA248 and pYA292 (EP 89900028.5). Vector pMEG-100 also contains the lower copy-number DNA polymerase I-dependent p15A origin of replication and the strong trc promoter derived from pYA810 and used in the pYA292 Asd$^+$ vector described in EP 89900028.5. The kanamycin resistance element of pMEG-100 was then removed by a partial SalI digest to produce pMEG-104, the ELVS vector shown in FIG. 4.

The second component of the ELVS is the host strain containing the regulator elements responsible for the response of the modified bacteria to the environmental conditions encountered. In the present example the host is MGN-392 or the sibling strain MGN-391, which contain a cI857PRc2 cartridge. The cI857PRc2 cartridge contains the bacteriophage lambda promoter right driven bacteriophage P22 c2 repressor gene and the bacteriophage lambda temperature sensitive repressor gene cI857. The cartridge is located between flanking portions of the *S. typhimurium* asd gene and replaces the chromosomal asd gene of the wild-type *S. typhimurium* strain χ3761. More specifically, the cI857PRc2 cartridge is a combination of a PCR amplified fragment of bacteriophage P22 derived from nucleotides 1 to 650 of the c2 gene (Sauer, R. et al., *Biochem.* 20:3591-3598 (1981), and a PCR amplified fragment of bacteriophage lambda, from nucleotides 37219 to 38035 of the lambda genome (Sanger, F., et al., *J. Mol. Biol.* 162:729-773 (1982), which contains the cI857 gene and the lambda promoter right. On the cartridge, the lambda promoter right drives expression of the P22 c2 gene. This cartridge has been inserted between the flanking portions of a defined deletion of the *S. typhimurium* asd gene lacking the portion of the asd gene between nucleotides 243 and 1460. This deletion prevents production of any β-aspartate semialdehyde dehydrogenase by the host strain MGN-392.

The function of the ELVS is demonstrated for both *Salmonella* and *E. coli* using the host strains MGN-392 for *S. typhimurium* (Table 3) and MGN-336 for *E. coli* (Table 1). MGN-392 was electroporated with either the Asd$^+$ vector pYA292, to produce MGN-401 (Table 1), or the ELVS expression vector pMEG-104, to produce MGN-417 (Table 3). MGN-336 was electroporated with the ELVS expression vector pMEG-104, to produce MGN-409 (Table 1). These strains were then grown for 12 to 16 hours in Lennox broth without aeration at 37° C. and dilutions plated onto Lennox agar followed by incubation at the temperature indicated for up to 72 hours. The plating efficiency, measured as colony forming units, observed at room temperature (25° C.) for MGN-417 is approximately 10,000 less than that observed for MGN-401, containing the Asd$^+$ vector, at the same temperature. The colonies observed after room temperature incubation of *E. coli* strain MGN-409 containing the ELVS vector pMEG-104 were extremely small, indicating poor growth survival (Table 4). The reduction obtained in plating efficiency of MGN-417 at 25° C. in the presence of DAP indicates that the lysis genes are functioning alone to cause greater than 95% killing.

TABLE 4

Plating Efficiency of Strains Containing Temperature Regulated ELVS Vectors[a]

| Strain (plasmid) | L agar at 25° C. CFU at 10$^{-4}$ dil. | L agar at 37° C. CFU at 10$^{-7}$ dil. | L agar + DAP at 25° C. CFU at 10$^{-7}$ dil. |
|---|---|---|---|
| *S. typhimurium* MGN-401 (pYA292) | >10,000 | 23 | N/A |
| *S. tiphimurium* MGN-417s (pMEG-104) | 1 mucoid | 67 | 1 mucoid |
| *E. coli* MGN-409e (pMEG-104) | ~10,000 very small | 36 | N/A |

[a]Colony forming units (CFU) of cultures diluted 10$^{-4}$ or 10$^{-7}$ plated on L agar or L agar + DAP, after 72 hrs incubation at designated temperature.

This reduction in viability is further demonstrated by the data in FIG. 6 for the *Salmonella* based ELVS in which MGN-417 (Table 3) fails to grow in complex liquid media at room temperature. Under these conditions, MGN-417 is unable to proliferate and exhibits a reduction in recoverable bacteria over a 24 hour period at the non-permissive temperature of 25° C., while still growing as well as MGN-401 (Table 1), the ELVS host MGN-392 containing the Asd+ vector pYA292, at the permissive temperature of 37° C.

Example 2

Figure 5:
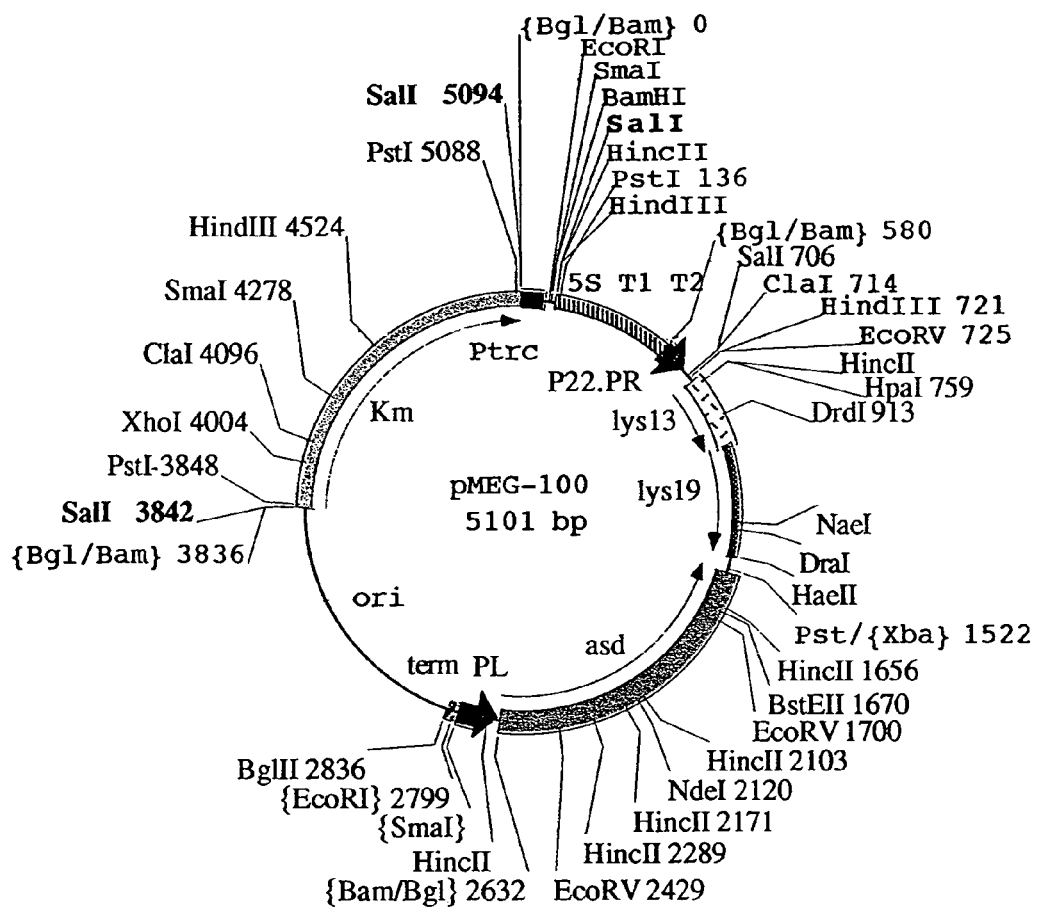
FIG. 5 is a diagram of vector pMEG-100. This vector is the same as vector pMEG-104 except that pMEG-100 contains a kanamycin resistance gene.

Restricted Transfer of Environmentally Limited Viability Vector DNA to Other Bacterial Hosts This example demonstrates the inability of bacterial hosts not containing the cI857PRc2 cartridge to maintain the Environmentally Limited Viability System vector, even at permissive temperatures. During the construction of pMEG-104, as described earlier, the vector pMEG-100, containing a kanamycin resistance gene, was produced (FIG. 5). Vector pMEG-100 and the tetracycline resistance plasmid pYA232 were co-purified from MGN-399 (Table 1). Vector pYA232 has a low copy-number pSC101 replicon that is compatible with the p15A origin of replication present on pMEG-100. The pool of plasmid DNA isolated from MGN-399 was then electroporated into an Asd− S. typhimurium host, χ3730, lacking the c2 repressor gene necessary for repression of the P22 lysis genes. In this strain, the lysis genes on pMEG-100 should limit the transformability by pMEG-100. The same pool of plasmid DNA was also electroporated into host strain MGN-391 (Table 1) to confirm the transformability of the DNA. The inability of the non-specific host, χ3730, to propagate the ELVS plasmid is evidenced by an approximately 3,000-fold drop in the number of electroporants obtained with pMEG-100 relative to pYA232 within the same DNA mix (Table 5). The CFU on L agar with tetracycline and DAP reveal the frequency of recovery of pYA232.

TABLE 5

Restriction of Plasmid Transfer to Non-permissive Hosts[a]
(CFU at $10^{-1}$ dilution)

| Strain | DNA | LA− | LA + Tet + DAP | LA + Km |
|---|---|---|---|---|
| x3730 | — | 0 | 0 | 0 |
| x3730 | pMEG-100 + pYA232 | 16 | >1,000 | 4 |
| MGN-391 | — | 0 | 0 | 0 |
| MGN-391 | pMEG-100 + pYA232 | >10,000 | ~1,000 | >10,000 |

[a] a mixture of pMEG-100 and pYa232 plasmid DNAs were isolated from S. typhimurium MGN-399 and used to transform the bacterial strains listed by electroporation.
[b] CFU (colony forming units) were determined by incubating dilutions spread on LA (Lennox agar) plates with or without tetracycline (Tet; 15 diaminopimelic acid (DAP; 50 μg/ml) or kanamycin (Km; 30 μg/ml); at 37° C.

Example 3

Construction of a Temperature-Regulated polA Host

This example describes the design of a Δasd Environmentally Limited Viability System in which the effectiveness of the Environmentally Limited Viability System is further ensured by employing a temperature regulated polA gene. The chromosomal polA gene has been altered to be expressed at 37° C. but not at temperatures below 30° C., thus preventing further replication of polA-dependent replicons containing the essential asd gene at the non-permissive temperature. As described above, the replication of plasmids with the p15A, pBR and pUC origins of replication are dependent on DNA polymerase I. These replicons are widely used in cloning vectors. The inability of these polA-dependent plasmids to replicate at temperatures below 30° C. will then result in plasmid vector loss from a population of cells growing at temperatures below 30° C. This will result in a loss of the ability to synthesize Asd, which in turn will reduce, and ultimately eliminate, synthesis of DAP. As described earlier, since DAP is an essential constituent of the rigid layer of the bacterial cell wall, the absence of DAP will cause DAP-less death and lysis of cells attempting to grow at temperatures below 30° C.

The S. typhimurium polA gene can be isolated from a library of 5 to 7 kb Sau3A fragments of S. typhimurium DNA cloned into a low copy-number of polA-independent vector, such as pSC101. The polA clones can be selected for their ability to rescue a polA-dependent plasmid when the library is electroporated into a temperature sensitive polA mutant χ1891 and cells are grown at 42° C.

Inverse PCR amplification of the S. typhimurium polA gene can then be performed using primers designed to eliminate the promoter region of polA but retain the Shine-Dalgamo sequence for translation initiation. The polA promoter will then be replaced with the bacteriophage lambda promoter left, which is regulated by the temperature-sensitive cI857 repressor.

This temperature regulated polA cartridge can then be transferred to a pir-dependent suicide vector, such as pMEG-011 and electroporated in a S. typhimurium host, such as MGN-392. By using S. typhimurium strains lacking the pir gene required for replication of the suicide vector, the suicide vector, with the temperature regulated polA gene, will integrate into the chromosome via a single recombinational event. Subsequent selection against the tetracycline resistance element on the suicide vector using fusaric acid will allow isolation of strains that have undergone a second crossover event replacing the wild-type polA gene with the temperature regulated polA gene. The resulting strain will thus provide temperature-regulated expression polA and temperature-regulated expression of c2 (from the cI857Pc2 cartridge inserted in the defined deletion of asd). The ELVS vector pMEG-104, or a derivative with a foreign gene inserted into the multiple cloning site downstream from Ptrc, could then be introduced into the strain. This strain will grow at 37° C. However, at temperatures below 30° C., the strain will undergo DAP-less death due to both the inability to maintain the plasmid vector with the asd gene and the inability to express asd, and the strain will also lyse due to the expression of phage lysis genes lys13 and lys19.

Example 4

Construction of a Chromosomally Based Environmentally Limited Viability System

The same components described in the construction of a vector based thermoregulated Environmentally Limited Viability System can be adapted to make a chromosomally based ELVS. The defined asd deletion containing the cI857PRc2 cartridge can first be introduced into a bacterial strain with properties desirable for its intended use, such as use as a vaccine or in a fermentation to produce a high-value product. The integration of the defined asd deletion containing the cI857PRc2 cartridge can be accomplished using the same procedure as described above for the construction of MGN-392. The thermoregulated asd lysis cartridge from pMEG-104 can then be transferred to a suicide vector containing a defined deletion of a selected gene. The chromosomal copy of the selected gene will be the target site of chromosomal integration for the asd lysis cartridge. If the host cell is a pathogen, it is preferred that the selected gene be a gene whose inactivation will attenuate the host cell and render it avirulent and immunogenic, as would be the case for a vaccine strain. Such selected genes could be, for example, cya, crp, phoP, aroA, aroC, aroD, ompR, htrA, and cdt. Alternatively, the selected gene could be a dispensable gene so that the engineered strain would have no noticeable defect. For fermentation strains, the selected gene could be chosen such that its inactivation will result in a fermentation production strain with improved production properties, such as a lessened ability to degrade expressed foreign gene products.

The suicide vector containing the asd lysis cartridge inserted into selected gene with the defined deletion can then be electroporated into a strain with a defined asd deletion containing the cI857PRc2 regulatory cartridge. Integration can be accomplished by selecting for first and second recombinational events as described above. The resulting strain will possess all components of the ELVS on the chromosome. If this strain were to be used as a vaccine, the expression of foreign antigens could be achieved by integrating the expression system for that foreign antigen into the chromosome. Alternatively, the gene for the foreign antigen could be contained on a plasmid vector lacking a drug resistance gene but containing a wild-type gene, such as purA or carA. Such a vector-borne gene would be essential for growth and replication inside an animal host of a vaccine strain with a ΔpurA or ΔcarA chromosomal mutation. Similar considerations could be used to establish a vector system for a fermentation production strain with a chromosomally located ELVS in order to achieve high-level expression of a foreign gene product.

Those skilled in the art will recognize, or be able to ascertain using no more than routine experimentation, many equivalents to the specific embodiments of the invention described herein. Such equivalents are intended to be encompassed by the following claims. All patents, patent applications, and publications mentioned herein, whether supra or infra, are hereby incorporated by reference.

We claim:

1. A method for inducing an immune response in a warm-blooded animal comprising administering to the animal a composition comprising a bacterial cell, wherein
    (a) the bacterial cell comprises an expression gene that encodes an antigen, and an Environmentally Limited Viability System,
    (b) the antigen is introduced into the animal,
    (c) the bacterial cell is viable when in the animal and non-viable when outside of the animal, and
    (d) the Environmentally Limited Viability System comprises an essential gene that is under the control of an environmentally regulatable control sequence, wherein
        (i) expression of the essential gene in the cell is essential to the viability of the cell,
        (ii) the essential gene is expressed when the cell is in the animal and is not expressed when the cell is outside of the animal,
        (iii) the essential gene is essential for metabolism, growth, cell wall integrity or cell membrane integrity of the bacterial cell, and
        (iv) the essential gene is a copy of a native chromosomal gene wherein the chromosomal copy of said native gene is inoperable.

2. The method of claim 1 wherein the antigen is selected from the group consisting of bacterial antigens, viral antigens, plant antigens, fungal antigens, insect antigens, and non-insect animal antigens.

3. The method of claim 1, wherein the composition is administered to mucosal surfaces of the animal.

4. The method of claim 1, wherein the bacterial cell is a member of the Enterobacteriaceae.

5. The method of claim 4, wherein the bacterial cell is an avirulent *Salmonella*.

6. The method of claim 5, wherein the avirulent *Salmonella* is an avirulent derivative of a pathogenic *Salmonella* that attaches to, invades and persists in the gut-associated lymphoid tissue or bronchial-associated lymphoid tissue.

7. The method of claim 1, wherein the essential gene is selected from the group consisting of
    genes encoding enzymes which catalyze steps in the biosynthesis of diaminopimelic acid (DAP) dapA, dapB, dapC, dapD, and dapE, the gene encoding alanine racemase (dal), the gene encoding D-alanyl D-alanine ligase (ddl), genes involved in fatty acid biosynthesis (fab), fatty acid degradation (fad), phospholipid synthesis (pls), a gene encoding a modification methylase, a gene encoding a DNA ligase, a gene encoding a DNA gyrase, and a gene encoding a phospholipase.

8. The method of claim 1, wherein the essential gene encodes an enzyme which catalyzes the biosynthesis of the cell wall and its precursors.

9. The method of claim 8, wherein the essential gene encodes an enzyme which catalyzes a step in the biosynthesis of diaminopimelic acid (DAP).

10. The method of claim 9, wherein the essential gene is the gene encoding β-aspartate semialdehyde dehydrogenase (asd).

11. The method of claim 1, wherein the system further comprises a lethal gene, wherein the expression of the lethal gene is lethal to the cell and the lethal gene is expressed when the cell is outside the animal but not when the cell is in the animal.

12. The method of claim 11, wherein the system further comprises a replication gene carried on a chromosome of the cell, the expression of which is required for replication of the vector, wherein the replication gene is expressed when the cell is in the animal and not expressed when the cell is outside the animal, wherein the cell is a member of the Enterobacteriaceae.

13. The method of claim 12, wherein the replication gene is the gene encoding deoxyribonucleic acid polymerase I, (polA).

14. The method of claim 11, wherein the lethal gene is selected from the group consisting of a member of the gef family, a plasmid maintenance gene, a gene encoding a nuclease, a gene encoding a phospholipase, a gene encoding an endolysin, a gene encoding a holin, and a gene encoding the tRNA with a wrong codon.

15. The method of claim 14 wherein the lethal gene is the combination of bacteriophage P22 lysis genes 13 and 19.

16. The method of claim 11, wherein the expression of the essential gene or the lethal gene is regulated by a trans regulatory element.

17. The method of claim 16, wherein the trans regulatory element is selected from the group consisting of a repressor, an antisense RNA, and an RNA polymerase.

18. The method of claim 11, wherein expression of the essential gene or the lethal gene is regulated by using promoters or regulatory elements that are regulated by temperature, or by other regulatory systems adapted to function in a temperature-dependent manner.

19. The method of claim 18, wherein the essential gene is regulated by being operatively linked to either
    (a) a virB promoter, wherein the bacterial cell further comprises a virF gene and promoter; or
    (b) a virF positive activator in combination with a promoter of yopH gene or a yadR gene.

20. The method of claim 19, wherein the essential gene is regulated by a bacteriophage lambda promoter left or right ($\lambda P_L$ or $\lambda P_R$) promoter with a temperature sensitive bacteriophage lambda cI857 repressor.

21. The method of claim 20, wherein the cI857 repressor is operatively linked to a Ptrc promoter.

22. The method of claim 19, wherein expression of the lysis gene is regulated by a bacteriophage P22 $P_R$ promoter operatively linked to a P22 c2 gene, wherein the P22 c2 gene is regulated by a $P_L$ promoter, and wherein the cell further comprises a chromosomal cI857 gene.

23. The method of claim 22, further comprising an essential gene operatively linked to a $\lambda P_L$ promoter.

24. The method of claim 23, wherein the cI857 repressor is inserted into an inactive chromosomal gene, wherein the inactive chromosomal gene is an inactive essential gene.

25. The method of claim 24, wherein the microbial cell is an avirulent *Salmonella*.

26. The method of claim 25, wherein the avirulent *Salmonella* is an avirulent derivative of a pathogenic *Salmonella* that attaches to, invades and persists in the gut-associated lymphoid tissue or bronchial-associated lymphoid tissue.

27. The method of claim 26, wherein the avirulent *Salmonella* further comprises an inactive gene selected from the group consisting of cya, crp, phoP, phoQ, ompR, galE, cdt, htrA, and a gene with a mutation that imposes a requirement for an aromatic amino acid or a vitamin.

28. The method of claim 24, wherein the extrachromosomal vector comprises pMEG-104.

29. The method of claim 28, wherein the extrachromosomal vector further comprises an expression gene.

30. The method of claim 29, wherein the expression gene encodes an antigen.

31. The method of claim 30, wherein the antigen is selected from the group consisting of a bacterial antigen, a viral antigen, a mycotic antigen, a parasitic antigen, a gamete specific antigen, and a tumor antigen.

32. The method of claim 1, wherein the antigen is selected from a group consisting of a bacterial antigen, a viral antigen, a mycotic antigen, a parasitic antigen, a gamete specific antigen, and a tumor antigen.

* * * * *